United States Patent
Kohrt et al.

(10) Patent No.: US 10,633,450 B2
(45) Date of Patent: *Apr. 28, 2020

(54) METHODS FOR ENHANCING ANTI-TUMOR ANTIBODY THERAPY

(71) Applicant: The Board of Trustees of the Leland Stanford Junior University, Stanford, CA (US)

(72) Inventors: Holbrook Kohrt, San Francisco, CA (US); Roch Houot, Rennes (FR); Ronald Levy, Stanford, CA (US); Arash Ash Alizadeh, San Mateo, CA (US); Matthew J. Goldstein, Hillsborough, CA (US); James Torchia, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/669,418

(22) Filed: Aug. 4, 2017

(65) Prior Publication Data

US 2018/0208670 A1  Jul. 26, 2018

Related U.S. Application Data

(63) Continuation of application No. 14/542,233, filed on Nov. 14, 2014, now Pat. No. 9,758,589, which is a continuation of application No. 13/513,523, filed as application No. PCT/US2010/059221 on Dec. 7, 2010, now Pat. No. 9,005,619.

(60) Provisional application No. 61/267,337, filed on Dec. 7, 2009, provisional application No. 61/287,067, filed on Dec. 16, 2009, provisional application No. 61/358,303, filed on Jun. 24, 2010.

(51) Int. Cl.
| | |
|---|---|
| C07K 16/28 | (2006.01) |
| A61K 39/395 | (2006.01) |
| C07K 16/32 | (2006.01) |
| C07K 16/30 | (2006.01) |
| G01N 33/574 | (2006.01) |
| A61K 39/00 | (2006.01) |

(52) U.S. Cl.
CPC ...... *C07K 16/2896* (2013.01); *C07K 16/2863* (2013.01); *C07K 16/2878* (2013.01); *C07K 16/2887* (2013.01); *C07K 16/2893* (2013.01); *C07K 16/3015* (2013.01); *C07K 16/3023* (2013.01); *C07K 16/3046* (2013.01); *C07K 16/3069* (2013.01); *C07K 16/32* (2013.01); *G01N 33/57492* (2013.01); *A61K 2039/507* (2013.01); *C07K 2317/21* (2013.01); *C07K 2317/24* (2013.01); *C07K 2317/73* (2013.01); *C07K 2317/732* (2013.01); *C07K 2317/75* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 8,475,790 B2 | 7/2013 | Jure-Kunkel et al. | |
| 8,716,452 B2 | 5/2014 | Jure-Kunkel et al. | |
| 9,005,619 B2 * | 4/2015 | Kohrt | C07K 16/2896 |
| | | | 424/144.1 |
| 9,758,589 B2 * | 9/2017 | Kohrt | C07K 16/2896 |
| 2003/0035790 A1 | 2/2003 | Chen et al. | |
| 2004/0018194 A1 | 1/2004 | Francisco et al. | |
| 2006/0127392 A1 | 6/2006 | de Romeuf et al. | |
| 2007/0071675 A1 | 3/2007 | Wu et al. | |
| 2008/0003225 A1 | 1/2008 | Vie et al. | |
| 2009/0087440 A1 | 4/2009 | Vicari et al. | |
| 2009/0175854 A1 | 7/2009 | Ashkenazi | |
| 2009/0214544 A1 | 8/2009 | Fischkoff et al. | |
| 2012/0321646 A1 | 12/2012 | Kohrt et al. | |
| 2013/0064831 A1 | 3/2013 | Humphrey et al. | |
| 2014/0044709 A1 | 2/2014 | Klencke et al. | |

FOREIGN PATENT DOCUMENTS

| | | |
|---|---|---|
| WO | 2011/146382 A1 | 11/2011 |
| WO | 2012/027536 A1 | 3/2012 |
| WO | 2014012479 A1 | 1/2014 |
| WO | 2014/055648 A1 | 4/2014 |
| WO | 2014/066532 A1 | 5/2014 |

OTHER PUBLICATIONS

Zingoni et al. Molecular Immunology 42 (2005) 451-454.*
Lin et al. (Blood 2008; 112: 699-707).*
Lui et al. J Clin Invest. 2008; 118(3): 1165-1175.*
Baltz et al. FASEB J. 21, 2442-2454 (2007).*
Bekiaris et al. Eur. J. Immunol. 2009; 39: 2800-2808.*
Smyth et al. Molecular Immunology 42 (2005) 501-510.*
Alderson et al., (2011) Journal of Biomedicine and Biotechnology, vol. 2011, Article ID 379123, 7 pages.
Dunne et al., J Immunol2001; 167:3129-3138.
Croft M., Semin Immunol. Mar. 5, 2014. pii: S1044-5323(14)00018-9. doi: 10.1016/j.smim.2014.02.005. [Epub ahead of print].
Croft M., Nat Rev Immunol. Apr. 2009;9(4):271-85.
Kohrt et al., Immunotherapy. May 2012(b); 4(5): 511-527.
Stagg et al., Proc Natl Acad Sci US A. Apr. 26, 2011;108(17):7142-7.
Cheng et al., Cellular & Molecular Immunology (2013) 10, 230-252.
Vinay et al., BMB Reports 2014; 47(3): 122-129.
James et al., Front Immunol. Dec. 23, 2013; 4: Article 481; 12 pages.
Kohrt et al., Blood 116:21 (Nov. 19, 2010); 2 pages.
Kohrtet al., Blood 117.8 (Dec. 30, 2010): 2423-32.
Lee et al., Immunol Res. Aug. 2011; 50(2-3): 248-254.

(Continued)

*Primary Examiner* — Ilia I Ouspenski
(74) *Attorney, Agent, or Firm* — Pamela J. Sherwood; Bozicevic, Field & Francis LLP

(57) ABSTRACT

Methods are provided to enhance the efficacy of antibody therapy directed to tumor cells.

17 Claims, 21 Drawing Sheets

(56) References Cited

OTHER PUBLICATIONS

Manair et al., Blood. Sep. 9, 2010; 116(10): 1726-1733. Prep. online Jun. 2, 2010.
Moran et al., Current Opinion in Immunology 2013, 25:230-237.
Murdoch et al., Current Opinion in Oncology 2008, 20:104-111.
North et al., J Immunol 2007; 178:85-94.
Sutlu et al., J Intern Med. Aug. 2009;266(2):154-81.
Melero et al., Clin Cancer Res 2013;19:1044-1053.
Lee et al., J Immunol 2006; 177:4464-4472.
Lee et al., Adv Exp Med Bioi. 2009; 647:120-9.
Kohrt et al. (Journal of Clinical Oncology, suppl. 1 28.15 American Society of Clinical Oncology (May 20, 2010)).
Kohrt et al. (Haematologica, suppl. 2 95: 305-306 (Jun. 13, 2010)).
Houot et al., "Therapeutic effect of CD137 immunomodulation in lymphoma and its enhancement by Treg depletion", Blood, Oct. 15, 2009, vol. 114, p. 3431-3438.
Capdevila; et al., "Anti-epidermal growth factor receptor monoclonal antibodies in cancer treatment", Cancer Treatment Reviews (Jun. 2009), 35(4):354-363.
Cartron; et al., "From the bench to the bedside: ways to improve rituximab efficacy", Blood (Nov. 1, 2004), 104 (9):2635-2642.
Hall; et al., "Current perspective—Trastuzumab", European Journal of Cancer (Jan. 2009), 45(1):12-18.
Houot; et al., Therapeutic effect of CD137 immunomodulation in lymphoma and its enhancement by Treg depletion, Blood (Oct. 2009), 114(16):3431-3438.
Kohrt; et al., "CD137 simulation enhances the antilymphoma activity of anti-CD20 antibodies", Blood (Feb. 2011), 117(8):2423-2432.
Kohrt; et al., "Simulation of natural killer cells with a CD137-specific antibody enhances trastuzumab efficacy in xenotransplant models of breast cancer", The Journal of Clinical Investigation (Mar. 2012), 122(3): 1066-1075.
Lin; et al., "Fc-dependent expression of CD137 on human NK cells: insights into "agonistic" effects of anti-CD137 monoclonal antibodies", Blood (Aug. 2008), 112(3):699-707.
Chen et al. "The B7-CD28 Family Molecules", Molecular Biology Intelligence Unit (2003), 1-153.
Jure-Kunkel et al. "Synergy between chemotherapeutic agents and CTLA-4 blockade in preclinical tumor models", Cancer ImmunolImmunother (2013), 62:1533-1545.
Kohrt et al. "Stimulation of natural killer cells with a CD 137-specific antibody enhances trastuzumab efficacy in xenotransplant models of breast cancer", J Clin Invest. (Mar. 2012), 122(3):1066-75.
Phase II Study for Previously Untreated Subjects With Non Small Cell Lung Cancer (NSCLC) or Small Cell Lung Cancer (SCLC), Bristol-Myers Squibb, ClinicaiTrials.gov (Jun. 2012), NCT00527735, 1-6, downloaded Aug. 4, 2014.
Choi; et al. "Mechanisms involved in synergistic anticancer immunity of anti-4-188 and anti-CD4 therapy", Cancer Res (Sep. 2007), 67(18):8891-8899.
Guo; et al. "Extracellular domain of 4-188L enhanced the antitumoral efficacy of peripheral blood lymphocytes 2 mediated by anti-CD3 x anti-Pgp bispecific diabody against human multidrug-resistant leukemia", CellImmunol (Feb. 2008), 251(2):102-108.
Ju; et al. "Eradication of established renal cell carcinoma by a combination of 5-fluorouracil and anti-4-188 monoclonal antibody in mice", Int J Cancer (Jun. 2008), 122(12):2784-2790.
Melero; et al. "Immunostimulatory monoclonal antibodies for cancer therapy", Nat Rev Cancer (Feb. 2007), 7 (2):95-106.
Shi; et al. "Augmented antitumor effects of radiation therapy by 4-188 antibody (8MS-469492) treatment", Anticancer Res (Sep.-Oct. 2006), 26(5A):3445-3453.
Takeda; et al "Combination antibody-based cancer immunotherapy", Cancer Sci (Sep. 2007), 98(9):1297-1302.
Teng; et al. "Combined natural killer T-cell based immunotherapy eradicates established tumors in mice", Cancer Res (Aug. 2007), 67(15):7495-7504.
Terme; et al. "Natural killer cell-directed therapies: moving from unexpected results to successful strategies" Nat Immunol (May 2008), 9(5):486-494.
Uno; et al "Eradication of established tumors in mice by a combination antibody-based therapy", Nat Med (Jun. 2006), 12(6):693-698.
Schneider-Merck et al., J Immunol2010; 184:512-520; Prepublished online Nov. 30, 2009.
Beano et al. Journal of Translational Medicine 2008, 6:25; 10 pages.
Melero et al., CellImmunol. 1998;190(2):167-172.
Wilcox et al., J Immunol. 2002;169(8):4230-4236.
Baessler et al., Blood. 2010;115(15):3058-3069; published online Dec. 14, 2009.
Liu et al., J. Clin. Invest. 118:1165-1175 (2008).
Placke et al., Clinical and Developmental Immunology, (2010), vol. 2010, Article ID 239083, 10 pages.
Schaer et al., Curr Opin Immunol. Apr. 2012; 24(2): 217-224.
Ogasawara et al., J Immunol 2002; 169:3676-3685.
Carbone et al., J. Exp. Med. vol. 185, No. 12, Jun. 16, 1997 2053-2060.
Rakhmilevich et al., Int Rev Immunol. Aug. 2012; 31 (4): 267-278.
Van Olffen, R.W., Dissertation, 2009, 41 pages. Adapted from Immunological Reviews 229(1), 216-31 (2009).
Becknell et al., (J Immunother 2008;31:685-692).
Ruby et al., Cancer ImmunolImmunother (2009) 58:1941-1947.
Advani et al., J Clin Oncol 27:4371-4377 (2009).
Campoli et al., Clin Cancer Res 2010;16:11-20. Published Online First Dec. 22, 2009.
Bhutani et al., Expert Opin. Bioi. Ther. (2013) 13(2):269-282.
Hallek M., Hematology Am Soc Hematol Educ Program. 2009:440-9.
Ito et al., Cancer Res 2004;64:8411-8419.
Betting et al., (J Immunother 2009;32:622-631).
Saler-Ardakani et al., Current Immunology Reviews, 2006, 2: 37-53.
Buechele et al., Eur. J. Immunol. 2012.42: 737-748.
Hirano et al., Cancer Res 2005;65:1089-1096.
Oilman R.O., Cancer Biother. Radiopharmaceut., v. 26, No. 1, 2011; 64 pages.
Cho et al., Korean J Lab Med. Apr. 2009; 29(2): 89-96.
Shifrin et al., Semin Immunol (2014), http://dx.doi.org/10.1016/j.smim.2014.02.007; 7 pages.
Knorr et al., Semin Immunol (2014), http://dx.doi.org/10.1016/j.smim.2014.02.002; 12 pages.
Sabry et al., Front Immunol. Nov. 25, 2013; v. 4, Article 408; 7 pages.
Marcais et al., Front Immunol. Dec. 12, 2013; v. 4, Article 450; 14 pages.

\* cited by examiner

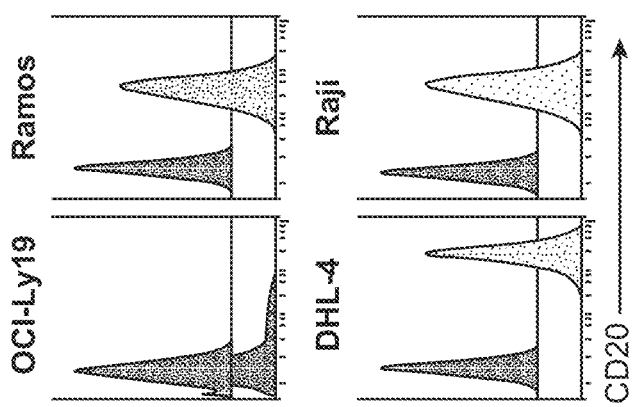
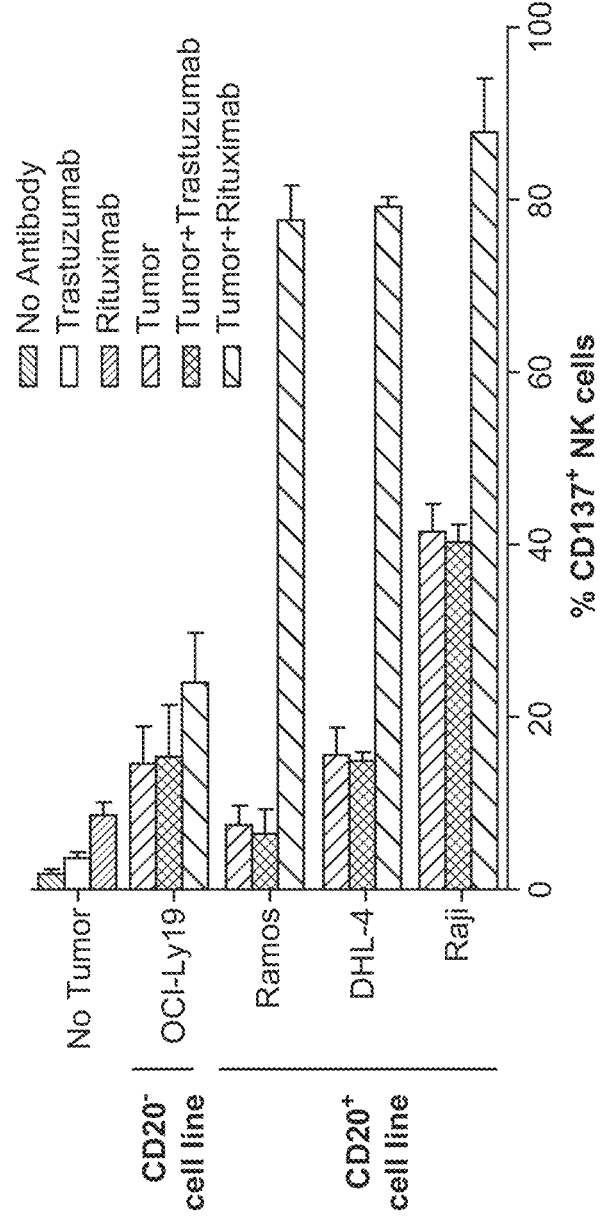
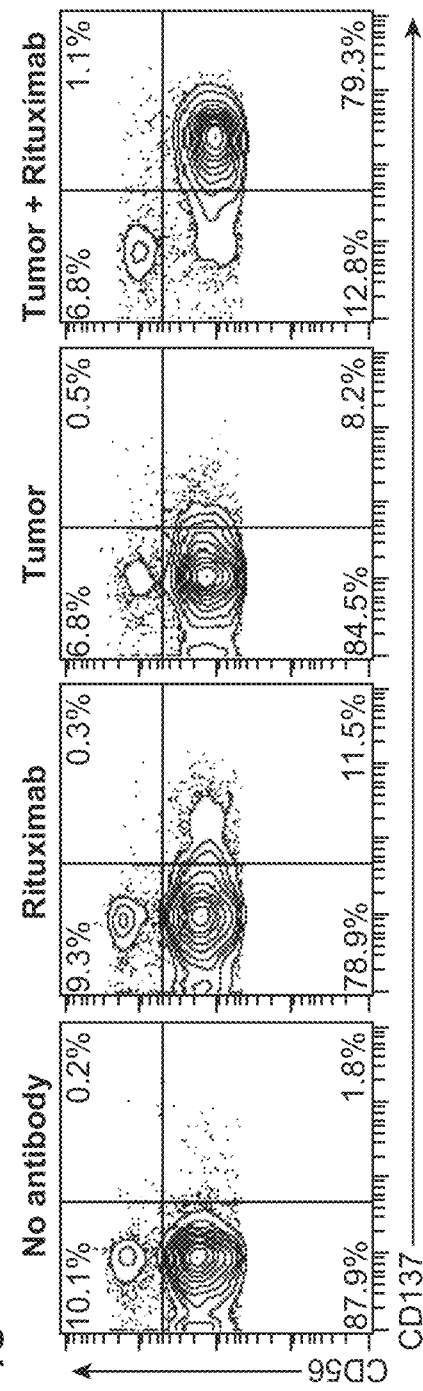
Figure 1A
Figure 1B
Figure 1C

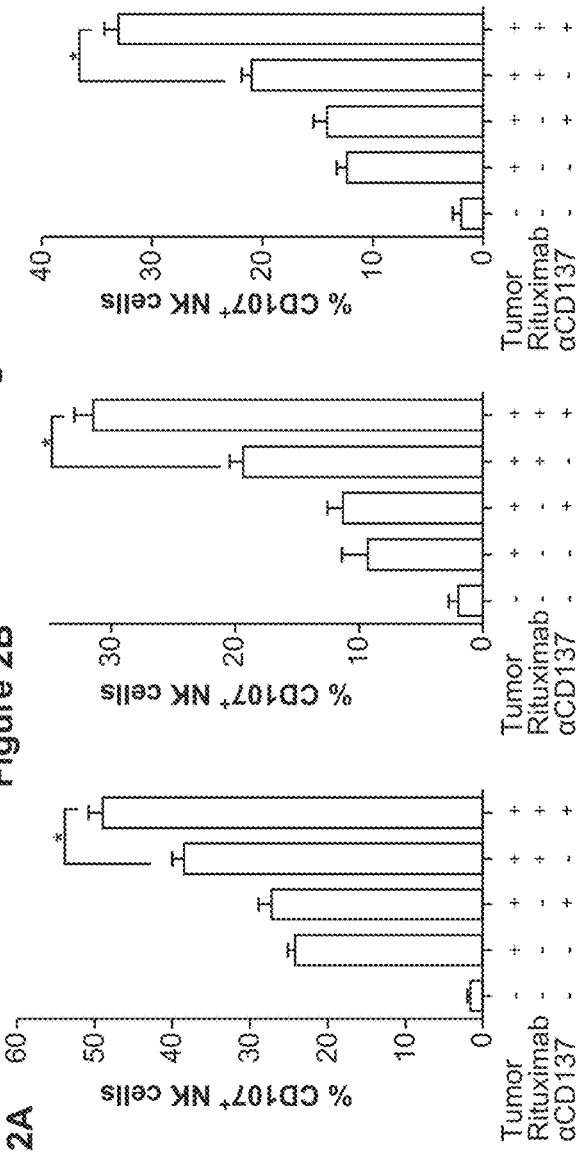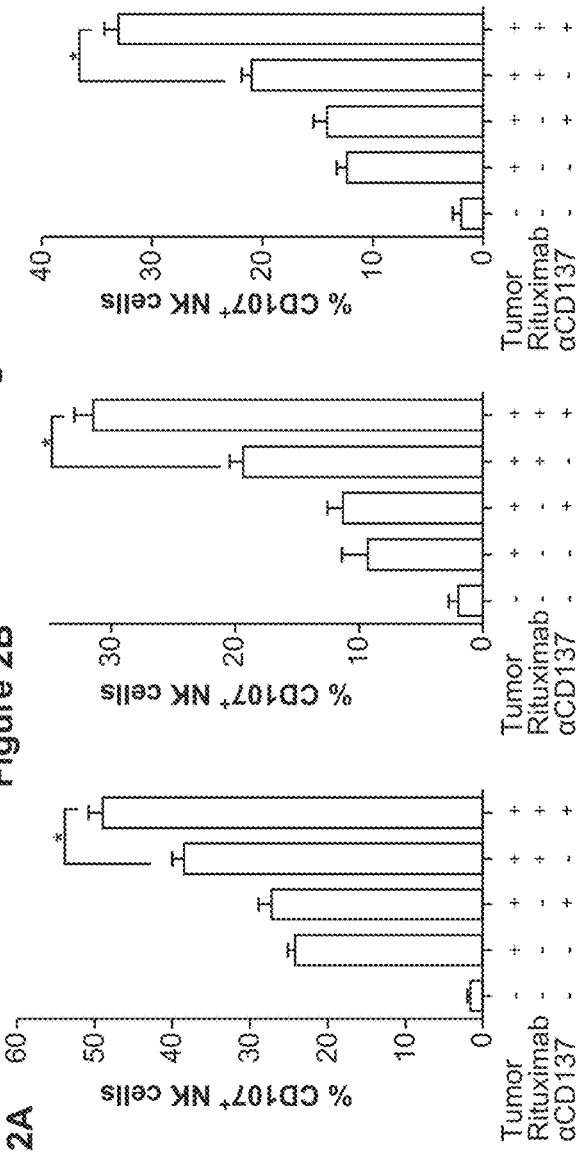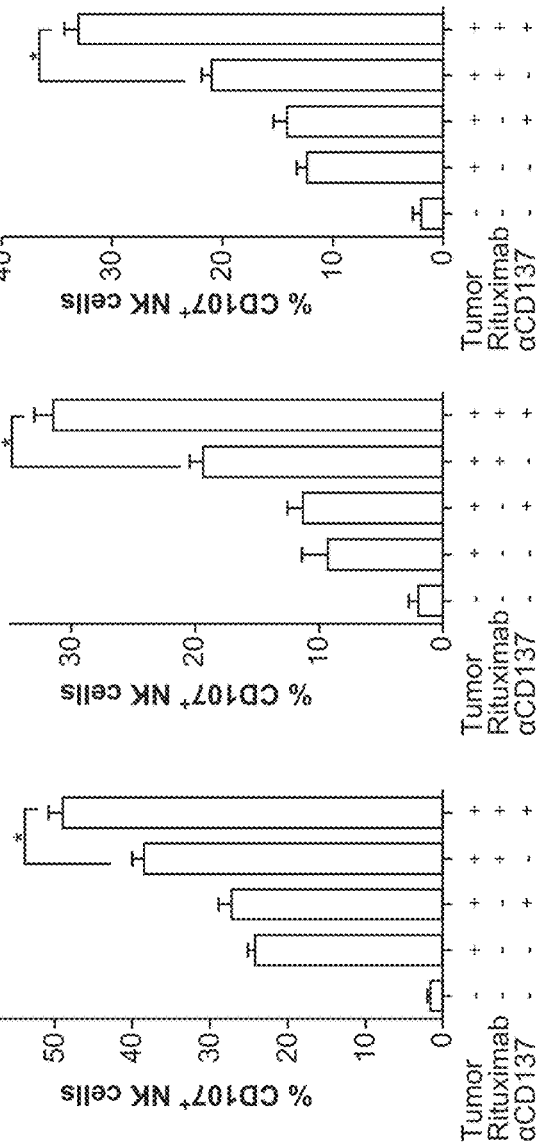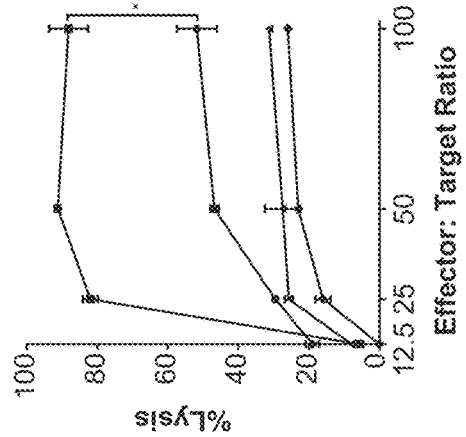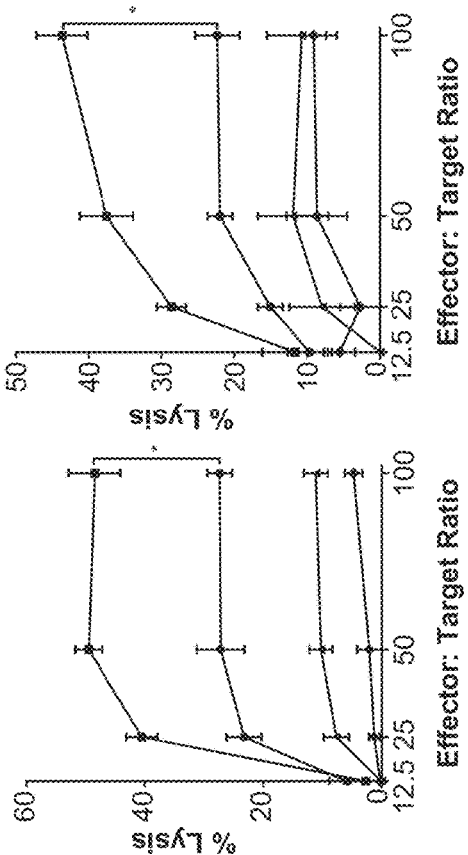
Figure 2A Figure 2B Figure 2C Figure 2D Figure 2E Figure 2F

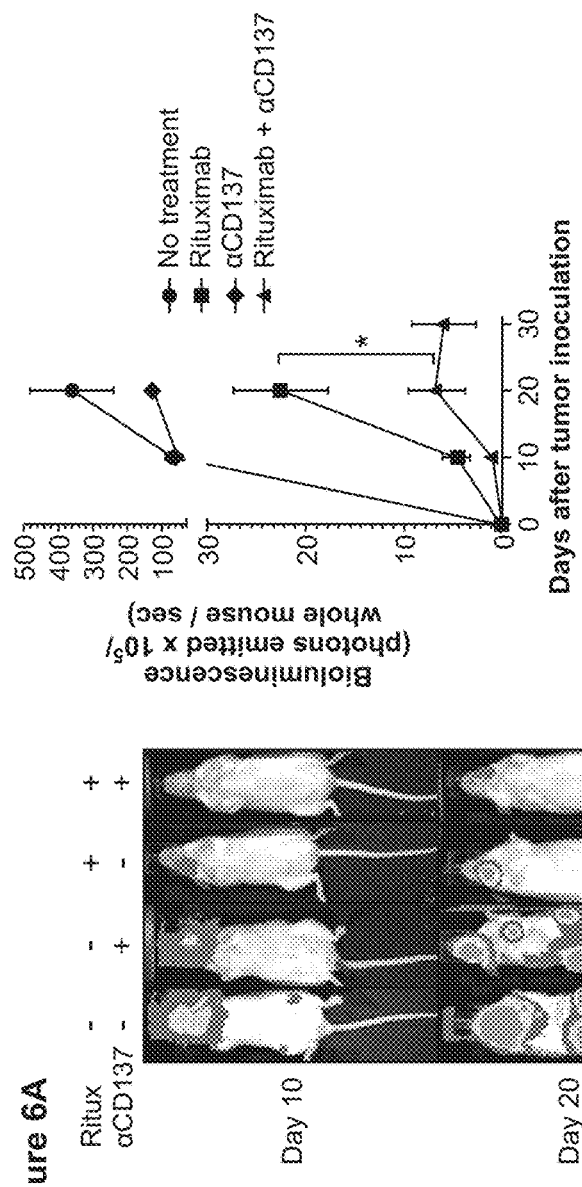
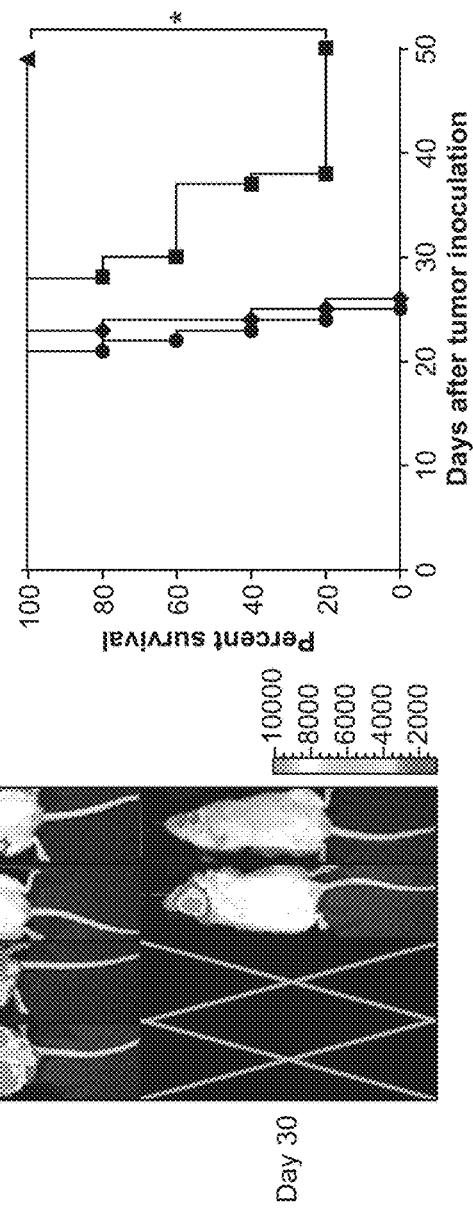
Figure 6A
Figure 6B
Figure 6C

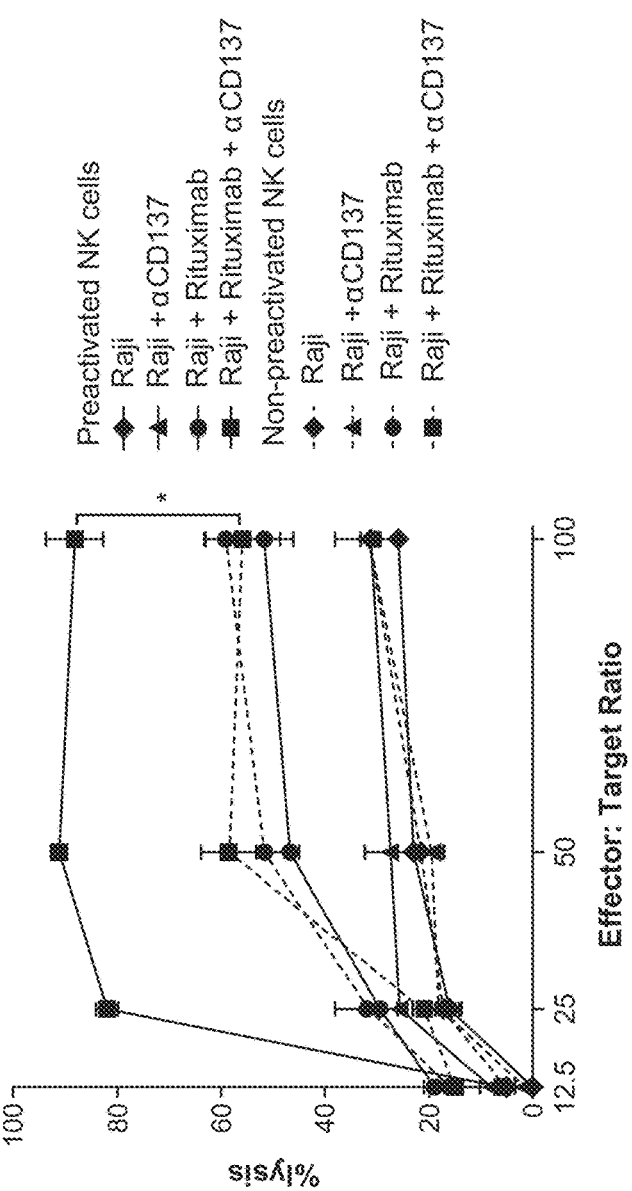
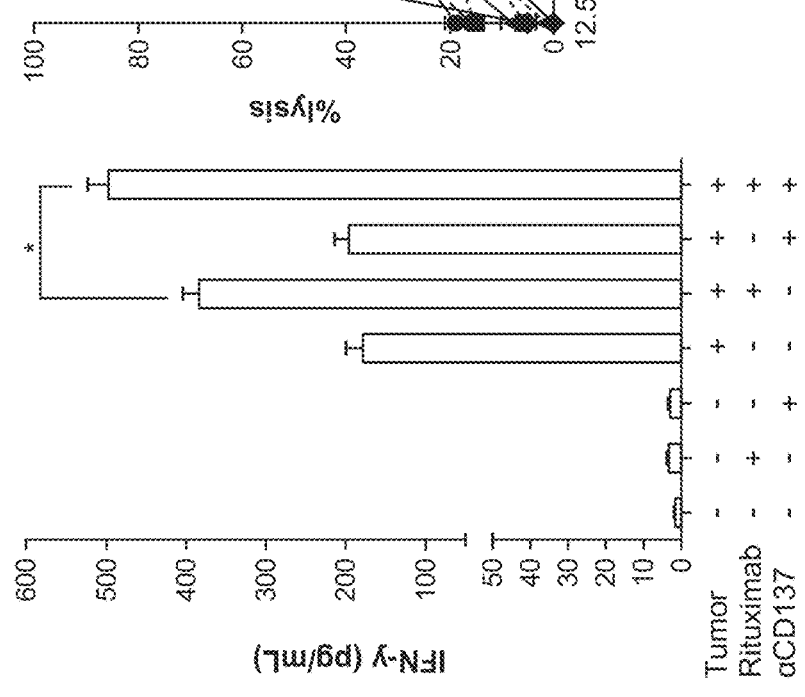
Figure 9A
Figure 9B

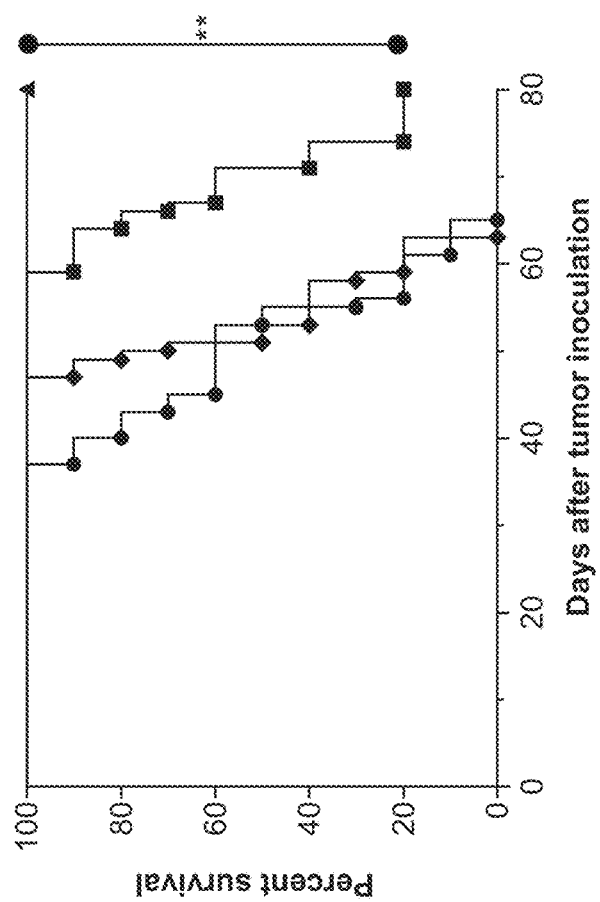
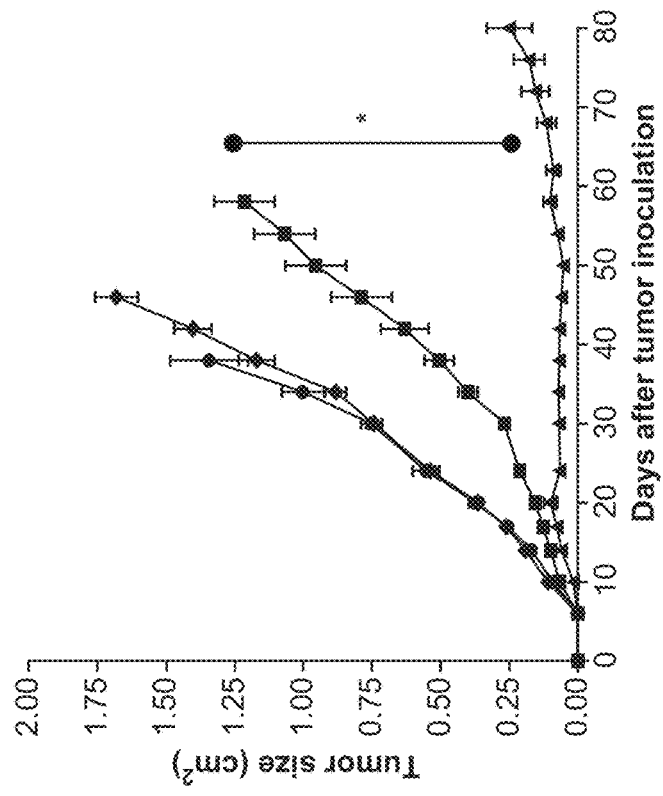
Figure 14A
Figure 14B

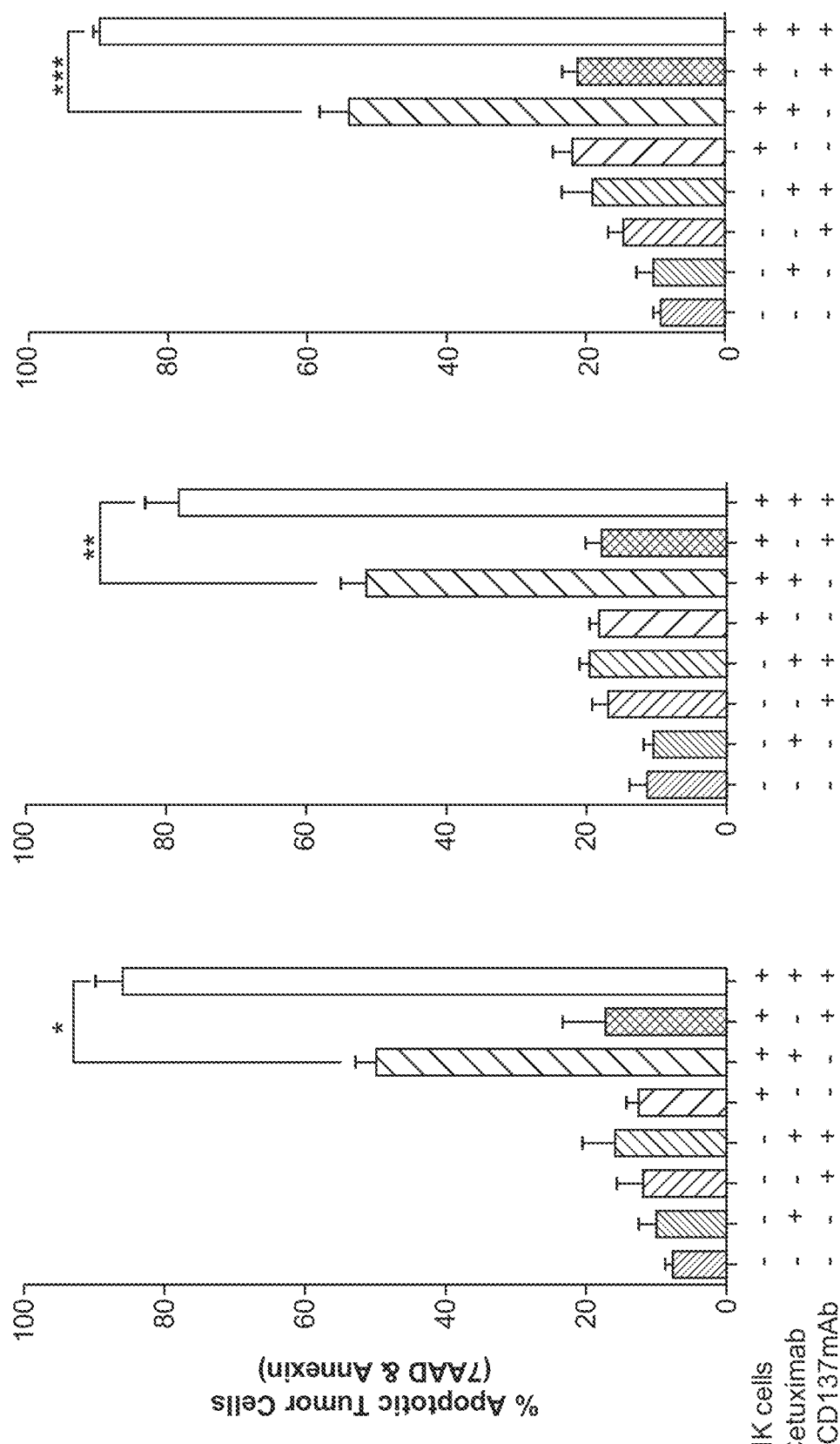

METHODS FOR ENHANCING ANTI-TUMOR ANTIBODY THERAPY

CROSS REFERENCE

This application claims benefit and is a Continuation of application Ser. No. 14/542,233 filed Nov. 14, 2014, which is a Continuation of application Ser. No. 13/513,523 filed Aug. 21, 2012, now U.S. Pat. No. 9,005,619 issued on Apr. 14, 2015, which is a 371 application and claims the benefit of PCT Application No. PCT/US2010/059221, filed Dec. 7, 2010, which claims benefit of U.S. Provisional Patent Application No. 61/358,303, filed Jun. 24, 2010, which claims benefit of U.S. Provisional Patent Application No. 61/287,067, filed Dec. 16, 2009, which claims benefit of U.S. Provisional Patent Application No. 61/267,337, filed Dec. 7, 2009, which applications are incorporated herein by reference in their entirety.

FEDERALLY SPONSORED RESEARCH AND DEVELOPMENT

This invention was made with Government support under contracts CA034233 and CA153248 awarded by the National Institutes of Health. The Government has certain rights in the invention.

BACKGROUND

Monoclonal antibody technology is among the most notable scientific advances in the last quarter century. Rapid translation of this research has prolonged the survival of thousands of patients with cancer. The first approved monoclonal antibody, rituximab, a murine-human chimeric IgG1 antibody against CD20, has become standard of care for patients with B cell lymphomas. Monoclonal antibodies against HER2 (trastuzumab) and the EGF receptor (cetuximab) have similarly changed the natural history of select patients with breast cancer, and both colorectal and head and neck cancers, respectively.

Despite the promising activity of monoclonal antibodies, the response rates among patients with either refractory or advanced cancer are suboptimal typically at less than 25%. Efforts to enhance the activity of monoclonal antibodies have focused on various combinations with cytotoxic chemotherapy. This largely ignores and may partially antagonize the immunologic mechanism by which monoclonal antibodies function.

Both adaptive and innate immune cells participate in the surveillance and the elimination of tumor cells. Among the innate cells are natural killer cells (NK cells), which constitute a major component of the innate immune system. NK cells play a major role in the rejection of tumors and cells infected by viruses. The cells kill by releasing small cytoplasmic granules of proteins called perforin and granzyme that cause the target cell to die by apoptosis.

Natural killer cell activity is tightly regulated, and requires an activating signal. For example, activation of the Fc receptor by antibodies allows NK cells to lyse cells through antibody-dependent cellular cytotoxicity (ADCC). Upon activation, the NK cell releases granules containing granzymes and perforin. Perforin forms pores in the cell membrane of the target cell, through which the granzymes and associated molecules can enter, inducing apoptosis.

ADCC is a primary mechanism by which tumor directed monoclonal antibody therapy works. However, conventional cytotoxic chemotherapies induce myelosuppression, decreasing the population of NK cells, thereby reducing the efficacy of ADCC. In contrast, therapies which augment NK cell function might offer the ability to improve activity of monoclonal antibodies without increasing toxicity to non-cancer cells. Clinically this is significant as an increasing population of cancer patients either due to older age, advanced disease, or prior therapies, are not candidates for conventional cytotoxic chemotherapy. The present invention addresses this issue.

SUMMARY OF THE INVENTION

Methods are provided to enhance the anti-tumor effect of monoclonal antibodies directed against tumor antigen(s). In the methods of the invention, ADCC function is specifically augmented, which in turn enhances target cell killing, by sequential administration of an antibody directed against one or more tumor antigens, and an agonistic antibody against one or several inducible costimulatory molecules on NK cells.

An individual diagnosed with a tumor is first administered a tumor-directed antibody. After a period of time NK cells which are innate immune effector cells critical for ADCC upregulate expression of inducible costimulatory molecules such as CD137, OX40, GITR, CD30 or ICOS. Subsequently, a second antibody is administered targeting the induced costimulatory molecule on NK cells (including but not limited to anti-CD137, anti-OX40, anti-GITR, anti-CD30 or anti-ICOS). In some embodiments, expression of the aforementioned costimulatory molecules is evaluated following administration of the tumor-directed antibody, in order to determine the optimal time for dosing the second agent. Alternatively a timing period is determined empirically, and generally applied. The combination of agents and their sequential administration is shown to provide for a level of tumor-specific, therapeutic synergy that is not observed with administration of the single agents alone. The method specifically enhances the anti-tumor function of monoclonal antibodies directed against tumor antigens. Because the second antibody targets costimulatory molecules that have been inducibly expressed on NK cells by the tumor-directed antibody, this methods allows specific stimulation of NK cells which are implicated in ADCC-mediated killing of the tumor cells, while sparing other NK cells, thereby limiting potential non specific side effects.

In some embodiments of the invention, the inducible costimulatory molecule is CD137. In such methods, an individual diagnosed with a tumor is first administered a tumor-selective antibody. After a period of time sufficient to upregulate expression of CD137 in immune system cells, a second agent is administered, which agent is an agonist of CD137. In some embodiments the level of CD137 expression on blood cells is determined prior to each administering step, where an increase in expression is indicative that the second agent may be administered.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1C. Rituximab induces CD137 upregulation on human NK cells following incubation with CD20-positive tumor B cells. Peripheral blood from three healthy donors was analyzed for CD137 expression on CD3⁻CD56⁺ NK cells after 24 hour culture with lymphoma cell lines and trastuzumab or rituximab. (FIG. 1A) shows the percentage of CD137⁺ cells among CD3⁻CD56⁺ NK cells from three healthy donors cultured with CD20⁻ lymphoma cell line (OCI-Ly19) or CD20-positive lymphoma cell lines (Ramos, DHL-4, Raji) cell lines. (FIG. 1B) shows CD20 surface expression on lymphoma cell lines (OCI-Ly19, Ramos, DHL-4 and Raji). Histograms were colored according to the log 10-fold increase in WI of lymphoma cell lines relative to isotype. (FIG. 1C) shows CD137 expression on NK cells subsets CD3⁻CD56$^{bright}$ and CD3⁻CD56$^{dim}$ from a representative healthy donor after 24 hour culture with the CD20-positive lymphoma cell line, Ramos and rituximab.

FIG. 2A-2F. Anti-CD137 agonistic mAb increases rituximab-mediated NK cell cytotoxicity on tumor cells. NK cells isolated and purified from the peripheral blood of healthy donors were analyzed for degranulation by CD107a mobilization after 24 hour culture with five conditions: media alone; CD20-positive lymphoma cell line (Raji, Ramos, or DHL-4); tumor and rituximab; tumor and anti-CD137 antibody; or tumor, rituximab, and anti-CD137 agonistic antibody (FIG. 2A, Raji, *p=0.01; FIG. 2B, Ramos, *p=0.003; FIG. 2C, DHL-4, *p=0.002). NK cell cytotoxicity on Raji, Ramos, and DHL-4 tumor cells was analyzed in chromium release assay (FIG. 2D-2F). Preactivated NK cells (as described in Material and Methods) were purified before being incubated with chromium labeled Raji, Ramos, and DHL-4 cells for 4 hours. (FIG. 2D-2F) shows percent lysis of target cells by chromium release at varying effector (activated NK cells):target (Raji) cell ratios cultured with media alone (♦), anti-CD137 (▲), rituximab (●), or rituximab and anti-CD137 (■) antibodies (FIG. 2D, Raji, *p=0.01; FIG. 2E, Ramos, *p=0.01; FIG. 2F, DHL-4, *p=0.009).

FIG. 3A-3B Post-tumor inoculation, mice then received either Rat IgG control on day 3 (●), anti-CD20 antibody on day 3 (■), anti-CD137 antibody on day 4 (♦), or anti-CD20 antibody on day 3 and anti-CD137 antibody on day 4 (▲). Mice (10 per group) were then monitored for tumor growth (FIG. 3A, *p<0.001) and overall survival (FIG. 3B, *p=0.048). FIG. 3C-3D show tumor growth and survival with identical treatment sequence, however with treatment delayed until day 8 post tumor inoculation. Mice received either Rat IgG control on day 8 (●), anti-CD20 antibody on day 8 (■), anti-CD137 antibody on day 9 (♦), or anti-CD20 antibody on day 8 and anti-CD137 antibody on day 9 (▲). Mice (10 per group) were then monitored for tumor growth (FIG. 3C, *p<0.001) and overall survival (FIG. 3D, *p<0.001).

(FIG. 5A) Peripheral blood cell subsets from lymphoma-bearing C57BL/6 mice 4 days post-tumor inoculation treated on day 3 with either IgG control or anti-CD20 antibody were analyzed for CD137 expression on CD3-NK1.1⁺ NK cells (NK), F4/80⁺ macrophages (Mφ), CD3⁺CD8⁺ T cells (CD8), and CD3⁺CD4⁺ T cells (CD4) (n=3 mice per group, *p=0.001). (FIG. 5B) Tumor-infiltrating lymphocytes from lymphoma-bearing C57BL/6 mice 7 days post-tumor inoculation treated on day 3 with either IgG control or anti-CD20 antibody were analyzed for CD137 expression on CD3-NK1.1⁺ NK cells (NK), F4/80⁺ macrophages (Mφ), CD3⁺CD8⁺ T cells (CD8), and CD3⁺CD4⁺ T cells (CD4) (n=3 mice per group, *p=0.012, NS=not significant). (FIG. 5C-5D) C57BL/6 mice were inoculated with 5×10⁶ BL3750 lymphoma tumor cells. Post-tumor inoculation mice received either Rat IgG control on day 3 (●), anti-Asialo-GM1 on days −1, 0, 5, 10, 15, 20, and 25 with anti-CD20 antibody on day 3 and anti-CD137 antibody on day 4 (■), liposomal (L.) clodronate on days −2, 0, 4, 8, 12, 16, 20, and 24 with anti-CD20 antibody on day 3 and anti-CD137 antibody on day 4 (▼), anti-CD8 mAb on days −1, 0, 5, 10, 15, 20, and 25 with anti-CD20 antibody on day 3 and anti-CD137 antibody on day 4 (♦), or anti-CD20 antibody on day 3 and anti-CD137 antibody on day 4 (▲). Mice (10 per group) were then monitored for tumor growth (FIG. 5C, *p=0.002) and overall survival (FIG. 5D, *p<0.001).

FIG. 6A-6C. Anti-CD137 agonistic mAb enhances anti-lymphoma activity of rituximab in vivo in a disseminated human lymphoma xenotransplant model. SCID mice were inoculated with 3×10⁶ luciferase-labeled Raji lymphoma tumor cells, intravenously through the retro-orbital sinus. Post-tumor inoculation, mice then received either Rat IgG control on day 3 (●), rituximab on day 3 (■), anti-CD137 antibody on day 4 (♦), or rituximab on day 3 and anti-CD137 antibody on day 4 (▲). Treatment was continued weekly for a total of 4 weeks. Luciferase imaging of representative mice 10, 20, and 30 days post treatment are shown (FIG. 6A). Mice (5 per group) were then monitored for quantified bioluminescence (FIG. 6B, *p=0.001) and overall survival (FIG. 6C, *p=0.013).

(FIG. 7A) shows CD16 and CD137 expression on CD3⁻CD56⁺ NK cells for a patient with marginal zone lymphoma (MZL) with 70% CTC. (FIG. 7B) shows the percentage of CD137⁺ cells among CD3⁻CD56⁺ NK cells in a cohort of 25 patients with follicular lymphoma (FL), chronic lymphocytic leukemia (CLL), MZL, mantle cell lymphoma (MCL), diffuse large B-cell lymphoma (DLBCL), and CD20-positive acute lymphoblastic leukemia (ALL). (FIG. 7C) shows correlation, R2=0.87, p<0.001, between the percentage of peripheral blood CTC and CD137 surface expression on CD3⁻CD56⁺ NK cells after 24 hour culture with rituximab from patient samples with FL (◉), CLL (●), MZL (☺), DLBCL (✺), and CD20-positive ALL (✪).

FIG. 9A-9B. Anti-CD137 agonistic mAb increases cytokine release and rituximab-mediated cytotoxicity of pre-activated NK cells. To evaluate NK cell interferon-γ secretion purified NK cells were isolated from healthy PBMCs and cultured for 24 hours together with rituximab (10 µg/mL) and irradiated (5,000 rads) lymphoma tumor cells (Raji) at a ratio of 1:1. After 24 hours, NK cells were isolated and assessed for purity (>90% purity as defined by CD3-CD56+ flow cytometry)(FIG. 9A-9B). Preactivated, purified NK cells were then cultured for 4 hours in media alone, or with anti-CD137 mAb (BMS-663513, 10 µg/mL) alone, rituximab (10 µg/mL) alone, or rituximab plus anti-CD137 mAbs (both at 10 µg/mL) and supernatant was harvested and analyzed by ELISA for interferon-γ (FIG. 9A, *p=0.027). NK cell cytotoxicity on Raji tumor cells was analyzed in chromium release assay with and without prior NK cell preactivation (FIG. 9B). Preactivated, and non-preactivated, purified NK cells were incubated with chromium-labeled Raji for 4 hours. Percent lysis of target cells by chromium release at varying effector (preactivated NK cells depicted in continuous line, and non-preactivated NK cells depicted in dashed line):target (Raji) cell ratios cultured with media alone (♦), anti-CD137 (▲), rituximab (●), or rituximab and anti-CD137 (■) antibodies (*p=0.024).

(FIG. 11A) shows the expression of CD69$^+$ and CD137$^+$ on CD3$^-$CD56$^+$ NK cells from a representative healthy donor after 24 hour culture with HER2$^+$ breast cancer cell line (BT474M1). (FIG. 11B) shows HER2 surface expression on breast cancer cell lines (MCF7, BT474M1, SKBR3, and HER18). Histograms were colored according to the log 10-fold increase in MFI of breast cancer cell lines relative to isotype. (FIG. 11C) shows CD137 expression from three healthy donors cultured on NK cells CD3$^-$CD56$^+$ after 24 hour culture with variably expressing HER2 breast cancer cell lines (MCF7, BT474M1, SKBR3, HER18).

(FIG. 12A-12C) shows percent of apoptotic target cells by annexin and 7AAD viability staining after culture with NK cells, tumor, media alone, anti-CD137, trastuzumab, or trastuzumab and anti-CD137 antibodies (FIG. 12A, MCF7 tumor line, FIG. 12B, BT474M1 tumor line *p=0.03; FIG. 12C, HER18, **p<0.01).

FIG. 14A-14B. Anti-CD137 agonistic mAb enhances anti-breast cancer activity of trastuzumab in-vivo. Nu/nu nude mice were inoculated with 5×10$^6$ BT474M1 breast tumor cells, subcutaneously, on the abdomen 1 day after subcutaneous injection of 0.72 mg/60 day release beta-estradiol pellet. (FIG. 14A-14B) Post-tumor inoculation, mice then received either Rat IgG control on day 3 (●), trastuzumab antibody on day 3 (■), anti-CD137 antibody on day 4 (♦), or trastuzumab on day 3 and anti-CD137 antibody on day 4 (▲) with each treatment repeated weekly for a total of three weeks. Mice (10 per group) were then monitored for tumor growth (FIG. 14A, *p<0.001) and overall survival (FIG. 14B, **p=.003).

FIG. 15A-15C) Post-tumor inoculation, mice then received either trastuzumab on day 3, or trastuzumab on day 3 and anti-CD137 antibody on day 4 with each treatment repeated weekly for a total of three weeks. FIG. 15A) Tumor model. FIG. 15B) Representative mice (3 of 10 per group) were then monitored for tumor growth. FIG. 15C) Tumor growth by treatment group and tumor type including MCF7 on left flank (○) and HER18 on the right flank (□) of mice treated with trastuzumab, and MCF7 on the left flank (●) and HER18 on the right flank (■) of mice treated with trastuzumab and anti-CD137 mAbs (*p<0.001).

(FIG. 17A) shows EGFR surface expression on head and neck cancer cell lines (103, SCC4, PC1, SCC6). Histograms were colored according to the log 10-fold increase in MFI of breast cancer cell lines relative to isotype. (FIG. 17B) shows CD137 expression from three healthy donors cultured on NK cells CD3⁻CD56⁺ after 24 hour culture with variably expressing EGFR head and neck cancer cell lines (SCC6, PC1, and SCC4).

FIG. 18A-18C. Anti-CD137 agonistic mAb increases cetuximab-mediated NK cell cytotoxicity on tumor cells as assayed by cell viability. Preactivated NK cells were purified before being incubated with SCC6, PC1, and SCC4 for 24 hours. (FIG. 18A-18C) shows percent of apoptotic target cells by annexin and 7AAD viability staining after culture with tumor alone or tumor and NK cells with media, cetuximab, anti-CD137, cetuximab and anti-CD137 antibodies (FIG. 18A, SCC6, *p=0.002; FIG. 18B, PC1, p=0.011; FIG. 18C, SCC4, *p=0.001).

(FIG. 21A) shows the phase 0, biomarker, trial schema (NCT01114256). (FIG. 21B) shows the percentage of CD137+ cells among fresh, peripheral blood CD3− CD56+ NK cells prior to and following cetuximab infusion.

DETAILED DESCRIPTION OF THE EMBODIMENTS

Figure 3A:
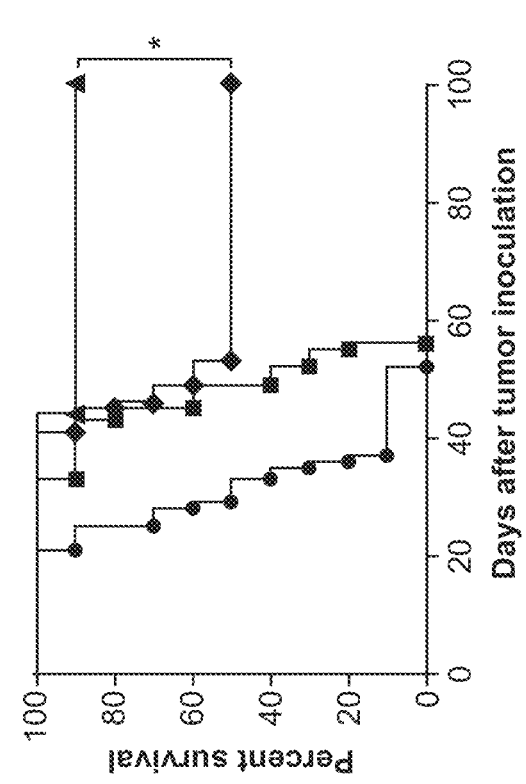
FIG. 3A-3D. Anti-CD137 agonistic mAb enhances anti-lymphoma activity of murine anti-CD20 mAb in-vivo. C57BL/6 mice were inoculated with 5×10⁶ BL3750 lymphoma tumor cells, subcutaneously, on the abdomen.
Figure 3B:
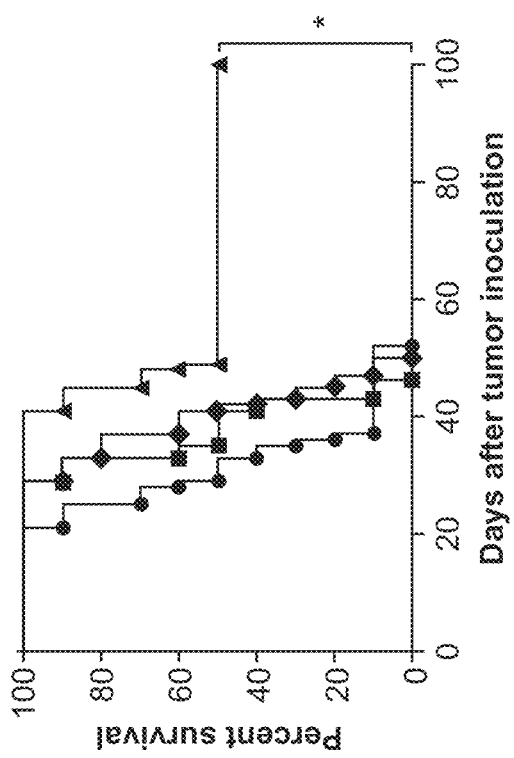
Figure 3C:
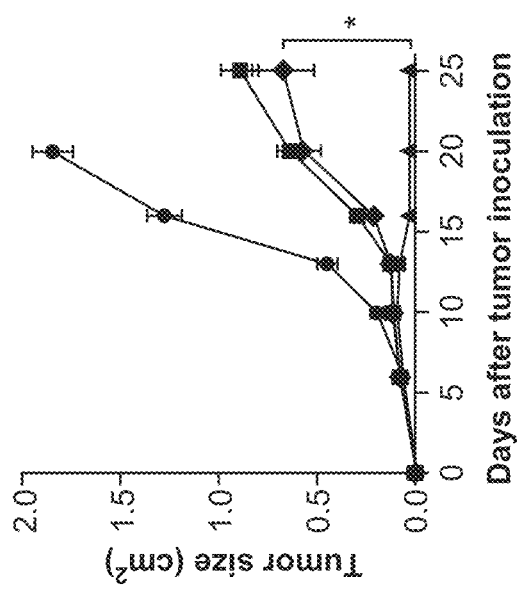
Figure 3D:
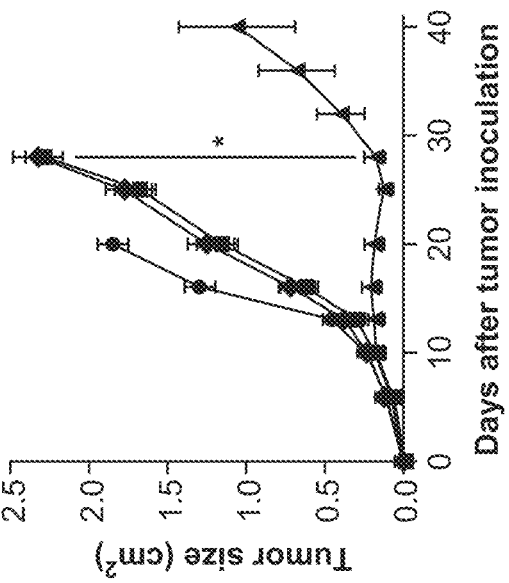

Methods are provided to enhance the anti-tumor effect of monoclonal antibodies directed against tumor antigens. In the methods of the invention, ADCC function is augmented and target cell killing is enhanced by sequential administration of a combination of antibodies. The combination of agents and sequential administration is shown to provide for synergistic effects, relative to the administration of the single agents. Administration of a tumor-directed antibody up-regulates the expression of inducible costimulatory molecules such as CD137, OX40, GITR, CD30 or ICOS on NK cells which are innate immune effector cells critical for ADCC. Subsequently, a second agonistic antibody is administered to target the induced costimulatory molecules (including but not limited to anti-CD137, -OX40, -GITR, -CD30 or -ICOS). In some embodiments, expression of the aforementioned costimulatory molecules following administration of the tumor-directed antibody is evaluated to determine the optimal time for dosing the second agent. Alternatively a timing period is determined empirically, and generally applied. Because the second antibody targets costimulatory molecules which have been inducibly expressed on NK cells by the tumor-directed antibody, this methods allows specific stimulation of NK cells that are implicated in ADCC-mediated killing of the tumor cells, while sparing other NK cells, thereby limiting potential non specific side effects.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Inducible costimulatory molecule. As used herein, an inducible costimulatory molecule is a polypeptide expressed on immune cells, including without limitation natural killer (NK) cells, which expression is induced or significantly upregulated during activation of NK cells. Activation of the costimulatory molecule enhanced the effector cell function, for example increasing ADCC mediated by the activated NK cells. Such inducible costimulatory molecules are known to those of skill in the art, and include, without limitation, CD137, OX40, GITR, CD30, ICOS, etc. Agonists of such molecules, including antibodies that bind to and activate the costimulatory molecule, are of interest for the methods of the invention. Many such costimulatory molecules are members of the tumor necrosis factor receptor family (TNFR). TNFR-related molecules do not have any known enzymatic activity and depend on the recruitment of cytoplasmic proteins for the activation of downstream signaling pathways.

CD137. CD137, which may also be referred to as Ly63, ILA or 4-1BB is a member of the tumor necrosis factor (TNF) receptor family. Members of this receptor family and their structurally related ligands are important regulators of a wide variety of physiologic processes and play an important role in the regulation of immune responses. CD137 is expressed by activated NK cells, T and B lymphocytes and monocytes/macrophages. The gene encodes a 255-amino acid protein with 3 cysteine-rich motifs in the extracellular domain (characteristic of this receptor family), a transmembrane region, and a short N-terminal cytoplasmic portion containing potential phosphorylation sites. Expression in primary cells is strictly activation dependent. The ligand for the receptor is TNFSF9. Human CD137 is reported to bind only to its ligand. Agonists include the native ligand (TNFSF9), aptamers (see McNamara et al. (2008) J. Clin. Invest. 118: 376-386), and antibodies.

CD134. OX40 (CD134) and its binding partner, OX40L (CD252), are members of the tumor necrosis factor receptor/tumor necrosis factor superfamily and are expressed on activated T cells as well as on a number of other lymphoid and non-lymphoid cells. OX40 and OX40L regulate cytokine production from T cells, antigen-presenting cells, natural killer cells, and natural killer T cells, and modulate cytokine receptor signaling.

GITR. Glucocorticoid-Induced TNFR-Related (GITR) protein belongs to tumor necrosis factor receptor/tumor necrosis factor superfamily and stimulates both the acquired and innate immunity. It is expressed in several cells and tissues, including T and Natural Killer (NK) cells and is activated by its ligand, GITRL, mainly expressed on antigen presenting cells and endothelial cells. GITR/GITRL system participates in the development of autoimmune/inflammatory responses and potentiates response to infection and tumors by mechanisms including NK-cell co-activation.

CD30. The transmembrane receptor CD30 (TNFRSF8) and its ligand CD30L (CD153, TNFSF8) are members of the tumor necrosis factor (TNF) superfamily and display restricted expression in subpopulations of activated immune cells. CD30 is a type I transmembrane glycoprotein of the TNF receptor superfamily. The ligand for CD30 is CD30L (CD153). The binding of CD30 to CD30L mediates pleiotropic effects including cell proliferation, activation, differentiation, and apoptotic cell death.

Inducible costimulator (ICOS). ICOS is a member of the CD28 family. ICOS expression, may be readily detectable resting, but it upregulated upon activation. ICOS and ICOS-L appear to be a monogamous pair. ICOS costimulation enhances effector functions.

"Inducible costimulatory molecule agonist" includes the native ligands, as described above, aptamers, antibodies specific for an inducible costimulatory molecule that activate the receptor, and derivatives, variants, and biologically active fragments of antibodies that selectively bind to an inducible costimulatory molecule. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein.

Fragments of the ligand or antibodies specific for an inducible costimulatory molecule, particularly biologically active fragments and/or fragments corresponding to functional domains, are of interest. Fragments of interest will typically be at least about 10 aa to at least about 15 aa in length, usually at least about 50 aa in length, but will usually not exceed about 200 aa in length, where the fragment will have a contiguous stretch of amino acids that is identical to the polypeptide from which it is derived. A fragment "at least 20 aa in length," for example, is intended to include 20 or more contiguous amino acids from, for example, an antibody specific for CD137, or from TNFSF9. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods. A "fusion" polypeptide is a polypeptide comprising a polypeptide or portion (e.g., one or more domains) thereof fused or bonded to heterologous polypeptide.

In some embodiments, the inducible costimulatory molecule agonist is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. In addition, the antibodies or antigen binding fragments may be produced by genetic engineering. Humanized, chimeric, or xenogeneic human antibodies, which produce less of an immune response when administered to humans, are preferred for use in the present invention.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ricin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

By "enhancing efficacy" is meant an increase in ADCC-mediated apoptosis of tumor cells compared to level of apoptosis observed with a single agent, e.g. a monoclonal antibody specific for a tumor cell. By synergistic, it is meant that a combination of agents provides for an effect greater than a single agent, which effect may be greater than the additive effect of the combined agents.

Tumor directed antibodies. A number of antibodies are currently in clinical use for the treatment of cancer, and others are in varying stages of clinical development. Antibodies of interest for the methods of the invention act through ADCC, and are typically selective for tumor cells, although one of skill in the art will recognize that some clinically useful antibodies do act on non-tumor cells, e.g. CD20.

There are a number of antigens and corresponding monoclonal antibodies for the treatment of B cell malignancies. One popular target antigen is CD20, which is found on B cell malignancies. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes.

Monoclonal antibodies useful in the methods of the invention, which have been used in solid tumors, include without limitation edrecolomab and trastuzumab (herceptin). Edrecolomab targets the 17-1A antigen seen in colon and rectal cancer, and has been approved for use in Europe for these indications. Its antitumor effects are mediated through ADCC, CDC, and the induction of an anti-idiotypic network. Trastuzumab targets the HER-2/neu antigen. This antigen is seen on 25% to 35% of breast cancers. Trastuzumab is thought to work in a variety of ways: downregulation of HER-2 receptor expression, inhibition of proliferation of human tumor cells that overexpress HER-2 protein, enhancing immune recruitment and ADCC against tumor cells that overexpress HER-2 protein, and downregulation of angiogenesis factors.

Alemtuzumab (Campath) is used in the treatment of chronic lymphocytic leukemia; colon cancer and lung cancer; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc. Cancers of interest include, without limitation, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as cervical, bladder cancer and renal cell carcinomas, head and neck cancers, gastro intestinal track cancers and nervous system cancers, benign lesions such as papillomas, and the like.

The phrase "solid tumor" as used herein refers to an abnormal mass of tissue that usually does not contain cysts or liquid areas. Solid tumors may be benign or malignant. Different types of solid tumors are named for the type of cells that form them. Examples of solid tumors are sarcomas, carcinomas, lymphomas etc.

Monoclonal antibodies directed against a specific cancer epitope, or combination of epitopes allows the targeting and/or depletion of cancer cell populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "recipient", "individual", "subject", "host", and "patient", used interchangeably herein and refer to any mammalian subject for whom diagnosis, treatment, or therapy is desired, particularly humans.

"Therapeutic target" refers to molecules expressed by the tumor cells and/or non tumor (immune) cells that can be targeted to induce or enhance antitumor activity.

Methods

Methods are provided to enhance the efficacy of cell killing induced by the administration of antibodies directed against tumor cells. An effective dose of a primary tumor-directed antibody is administered to a patient, which induces the upregulation of inducible costimulatory molecules such as CD137, OX40, GITR, CD30 or ICOS on NK cells, which are innate immune effector cells critical for ADCC. Subsequently, an effective dose of a second agonistic antibody against one of these molecules, including but not limited to CD137, OX40, GITR, CD30 or ICOS) is administered to said individual, where the second antibody is sufficient to enhance ADCC killing of tumor cells targeted by the first antibody. Because the second antibody targets costimulatory molecules that have been inducibly expressed on NK cells by the tumor-directed antibody, this methods allows specific stimulation of NK cells that are implicated in ADCC-mediated killing of the tumor cells, while sparing other NK cells, thereby limiting potential non-specific side effects.

In some embodiments the level of costimulatory molecules (including but not limited to CD137, OX40, GITR, CD30 or ICO) induced by the tumor-directed antibody is determined in a patient sample, usually a patient blood sample or cellular fraction thereof. As a baseline, the level of costimulatory molecules may be determined in a sample prior to administering the tumor-directed antibody, and the increase in expression following administration of the tumor-directed antibody determined.

In some embodiments of the invention, an effective dose of a tumor-selective antibody is administered to a patient, following which sufficient time is elapsed for an upregulation of CD137 expression on immune system cells, particularly NK cells. The sufficient time is usually at least about 12 hours, more usually at least about 18 hours, and usually at least about 24 hours, and may be at least about 2 days, at least about 3 days, and not more than about 5 days, usually not more than about 4 days. Following upregulation of CD137, an effective dose of a CD137 agonist is administered to said individual, where the agonist is sufficient to enhance ADCC killing of tumor cells targeted by the first antibody. In some embodiments the level of CD137 is determined in a patient sample, usually a patient blood sample or cellular fraction thereof. As a baseline, the level of CD137 may be determined in a sample prior to administering the tumor-selective antibody, and the increase in expression following administration of the tumor-selective antibody determined. A desirable increase in expression of CD137 on NK cells is at least about 1.5-fold, at least about 2-fold, or higher. An increase in expression when measured in overall blood cells may be lower due to the number of contaminating non-responsive cells.

"Reducing growth of cancer cells" includes, but is not limited to, reducing proliferation of cancer cells, and increasing apoptosis of tumor cells. Whether a reduction in cancer cell growth has been achieved can be readily determined using any known assay, including, but not limited to, [$^3$H]-thymidine incorporation; counting cell number over a period of time; detecting and/or measuring a marker associated with the cancer of interest, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

Formulations

Therapeutic formulations comprising one or more antibodies utilized in the methods of the invention may be prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular cancer being treated, the clinical condition of the individual patient, the site of delivery of the agent, the method of administration, the scheduling of administration, and other factors known to medical practitioners. The "therapeutically effective amount" of the antibody to be administered will be governed by such considerations.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for route of administration.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies as described above. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Antibodies and agonists suitable for use in the methods of the invention may be provided in a kit form, for example presented in a pack or dispenser device containing one or more unit dosage forms containing the active ingredients. Such a pack or device may, for example, comprise metal or plastic foil, such as a blister pack. The pack or dispenser device may be accompanied by instructions for administration. Compositions comprising agents useful in the methods of the invention may be formulated in a compatible pharmaceutical carrier may also be prepared, placed in an appropriate container, and labeled for treatment of an indicated condition. Suitable conditions indicated on the label may include treatment of cancer. Kits may also comprise a unit suitable for measuring expression of an inducible costimulatory molecule on NK cells, e.g. including detectable labeled reagent that specifically binds to an inducible costimulatory molecule, and references for expression, and the like as known in the art.

EXPERIMENTAL

The paradigm of cancer treatment prior to a decade ago was limited to conventional cytotoxic chemotherapy with the assumption of increased sensitivity to agents such as cell cycle inhibitors or DNA damaging agents by rapidly proliferating tumor cells. This paradigm changed in 1997 with the Food and Drug Administration approval of rituximab, the first therapeutic monoclonal antibody, which targets the surface marker CD20 for the treatment of non-Hodgkin lymphoma. Monoclonal antibodies have unique advantages over conventional cytotoxic chemotherapy—well-tolerated with less systemic toxicity, selectivity to tumor with minimal off-target effects, and ability to target slowly proliferating cells not undergoing frequent mitosis.

Following the approval of rituximab, trastuzumab, a humanized IgG1 antibody against HER2 (human epidermal growth factor receptor 2), was approved in 1998 for HER2$^+$ breast cancer. In 2004 cetuximab, a chimeric IgG1 antibody targeting the EGFR (epidermal growth factor receptor), was approved for colorectal cancer. In 2006 cetuximab was also approved for treatment of head and neck cancers. As evidenced by the recent identification of HER2$_+$ gastric and esophageal cancer, cancer therapies are now focused on discovery of both novel and known targets to which new or current antibodies can be aimed.

In contrast to conventional chemotherapy, monoclonal antibodies demonstrate minimal direct cytotoxicity. Though evidence supports multiple mechanisms of antibody function, a major mechanism of antitumor activity is through antibody dependent cell-mediated cytotoxicity (ADCC). Cytotoxicity occurring by ADCC is mediated by natural killer (NK) cells or macrophage/monocytes bearing an Fc receptor which binds to the antibody-targeted tumor cell. NK cell Fc receptor binding to antibody activates the NK cell resulting in release of cytokines and cytotoxic granules which trigger apoptosis in the antibody-targeted tumor cell. Increased NK cell function augments ADCC and results in improved antitumor activity.

The present invention identifies costimulatory molecules that are inducibly expressed on NK cells, which are innate effector cells critical for ADCC following recognition of antibody-coated tumor cells. Following up-regulation by the tumor directed antibody, these costimulatory molecules (including but not limited to CD137, OX40, GITR, CD30 or ICOS) can subsequently be targeted with agonistic antibodies to enhance ADCC mediated by these effector cells. Given the increasing number of tumor target-specific antibodies, this has therapeutic implications for any cancer type directly targeted by a monoclonal antibody.

The clinical benefit of agonistic antibodies that enhance NK cell function is limited only by the number of targets expressed by tumor cells and target-specific antibodies. Given the impact of rituximab, trastuzumab and cetuximab over the prior decade, target and antibody discovery efforts are likely to continue to be an area of active research. Though application of agonistic NK cell antibodies will extend beyond non-Hodgkin lymphoma, breast cancer, colorectal and head and neck cancers, these four demonstrate the magnitude of clinical benefit.

Antibody coated tumor cells trigger the activation of NK cells, whose killing activity can then be stimulated by a second activating antibody against CD137. The addition of agonistic anti-CD137 antibody is a general approach to enhance the therapeutic effect of any anti-tumor antibody.

EXAMPLE 1

Increased NK cell expression of CD137 occurs following NK cell exposure to CD20$^+$ lymphoma coated with rituximab. Targeting CD137 with an agonistic antibody to enhance antitumor ADCC is dependent upon its increased surface expression on NK cells following their exposure to antibody coated tumor cells. Because the second antibody targets a costimulatory molecule (CD137) which is inducibly expressed on NK cells by the tumor-directed antibody (rituximab, trastuzumab), this methods allows specific stimulation of NK cells which are implicated in ADCC-mediated killing of the tumor cells (lymphoma, breast cancer), while sparing other NK cells, thereby limiting potential non specific side effects.

We isolated peripheral blood mononuclear cells (PBMCs) from patients with circulating $CD20^+$ tumor cells due to chronic lymphocytic leukemia (CLL), marginal zone lymphoma (MZL), and $CD20^+$ acute lymphoblastic leukemia (ALL). PBMCs were analyzed by flow cytometry after culture with trastuzumab or rituximab. Percent $CD137^+$ NK cells increased from 1-2% at baseline to 22-43% with concurrent downregulation of CD16 (the Fc receptor) following culture with rituximab. This appeared antibody dependent since no activation occurred following culture with trastuzumab. As shown in FIGS. 1A-1C, Rituximab induces CD137 upregulation on human NK cells following incubation with CD20-positive tumor B cells. Peripheral blood from three healthy donors was analyzed for CD137 expression on $CD3^-CD56^+$ NK cells after 24 hour culture with lymphoma cell lines and trastuzumab or rituximab.

Anti-CD137 agonistic mAb increases rituximab-mediated NK cell cytotoxicity on tumor cells, as shown in FIGS. 2A-2F. NK cells isolated and purified from the peripheral blood of healthy donors were analyzed for degranulation by CD107a mobilization after 24 hour culture with five conditions: media alone; CD20-positive lymphoma cell line (Raji, Ramos, or DHL-4); tumor and rituximab; tumor and anti-CD137 antibody; or tumor, rituximab, and anti-CD137 agonistic antibody. Shown in FIGS. 3A-3D, there is also an enhancement of anti-lymphoma activity with anti-CD137 agonistic mAb.

Figure 4A:
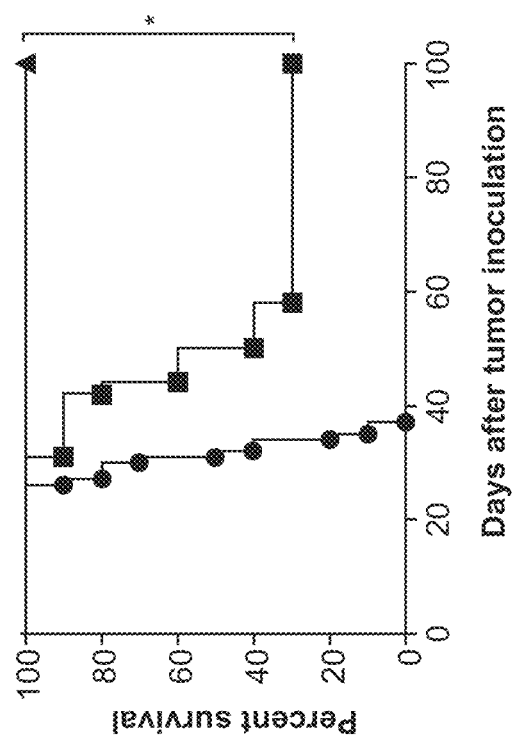
FIG. 4A-4B. Anti-CD20 and anti-CD137 mAbs combination activity requires appropriate sequence of mAb administration. C57BL/6 mice were inoculated with 5×10⁶ BL3750 lymphoma tumor cells, subcutaneously, on the abdomen. Post-tumor inoculation, mice then received either Rat IgG control on day 3 (●), anti-CD20 mAb on day 3 and anti-CD137 mAb on day 4 (▲), or anti-CD20 mAb on day 3 and anti-CD137 mAb on day 3 (■). Mice (10 per group) were then monitored for tumor growth (FIG. 4A, *p<0.001) and overall survival (FIG. 4B, * p=0.001).
Figure 4B:
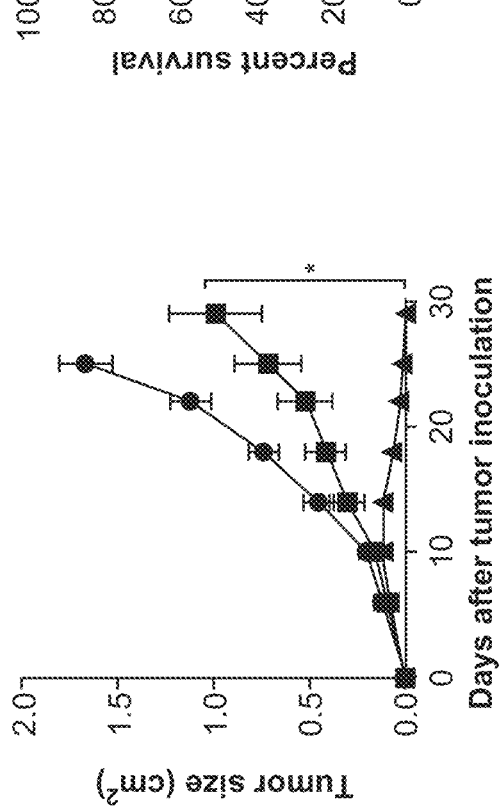
Figure 5A:
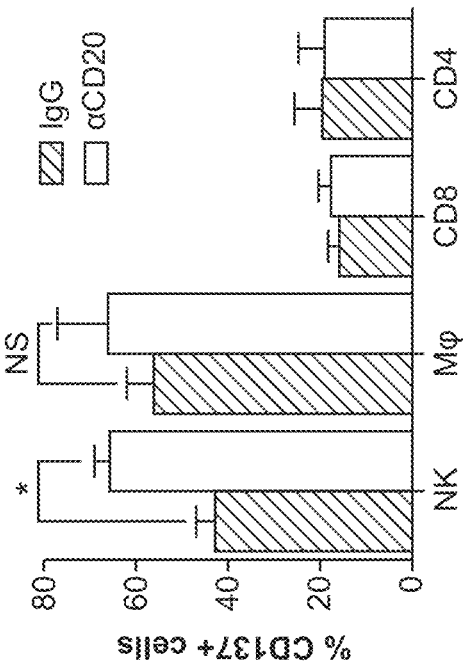
FIG. 5A-5D. Enhancement of the anti-lymphoma activity of anti-CD20 mAb by anti-CD137 agonistic mAb is dependent on NK cells and macrophages.
Figure 5B:
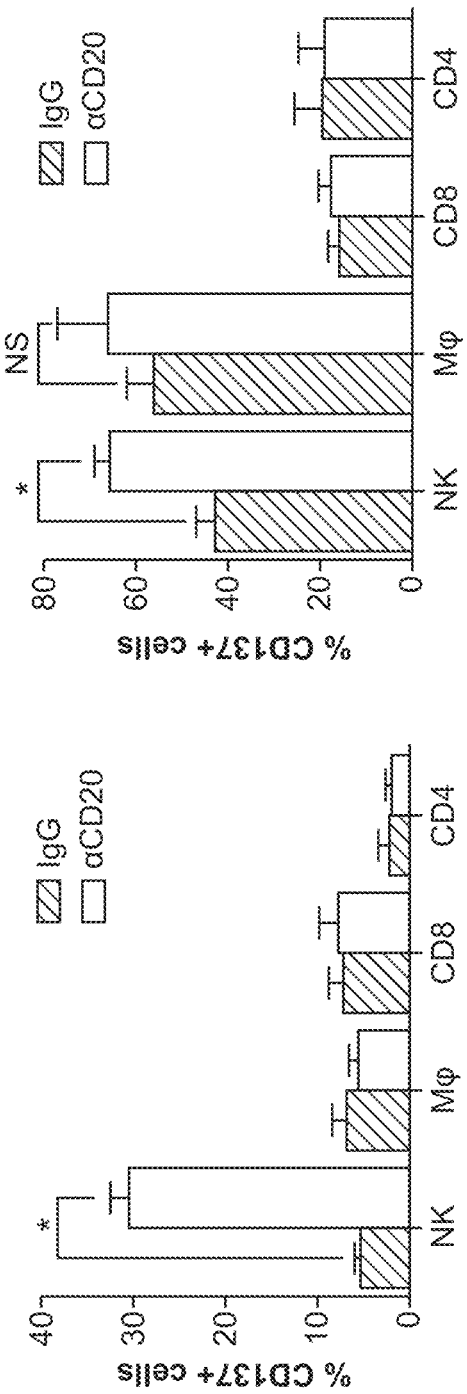
Figure 5C:
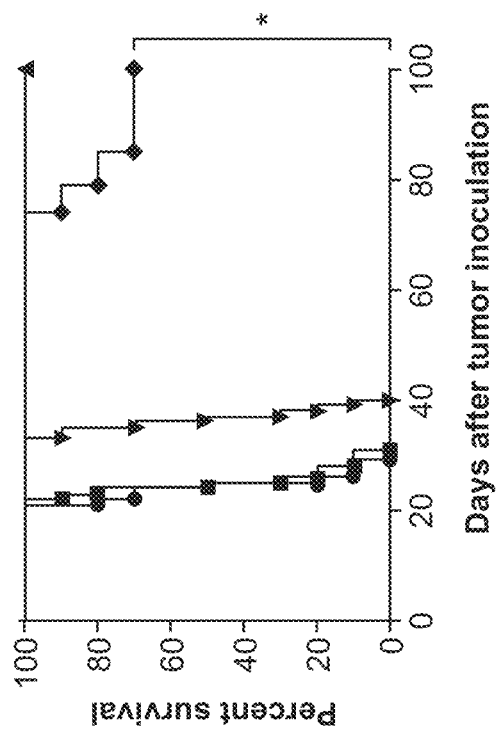
Figure 5D:
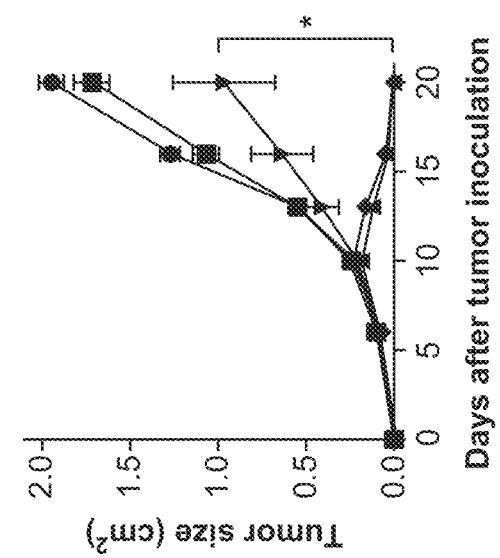

Anti-CD20 and anti-CD137 mAbs combination activity requires appropriate sequence of mAb administration, as shown in FIGS. 4A-4B, and is dependent on NK cells and macrophages. Shown in FIGS. 5A-5D, peripheral blood cell subsets from lymphoma-bearing C57BL/6 mice 4 days post-tumor inoculation treated on day 3 with either IgG control or anti-CD20 antibody were analyzed for CD137 expression on $CD3-NK1.1^+$ NK cells (NK), $F4/80^+$ macrophages (Mφ), $CD3^+CD8^+$ T cells (CD8), and $CD3^+CD4^+$ T cells (CD4); Tumor-infiltrating lymphocytes from lymphoma-bearing C57BL/6 mice 7 days post-tumor inoculation treated on day 3 with either IgG control or anti-CD20 antibody were analyzed for CD137 expression on $CD3-NK1.1^+$ NK cells (NK), $F4/80^+$ macrophages (Mφ), $CD3^+CD8^+$ T cells (CD8), and $CD3^+CD4^+$ T cells.

The synergy of anti-CD20Ab and anti-CD137Ab therapy observed in the syngeneic murine model is validated by testing the activity of anti-CD137Ab with rituximab, trastuzumab, and cetuximab in xenograft athymic, nude mouse models. This model has been previously used for preclinical testing of rituximab, trastuzumab, and cetuximab. In the lymphoma model, Balb/c nude nu/nu mice are inoculated on day 0 with $3\times10^6$ Raji cells transfected with Firefly Luciferase, and treated with rituximab (10 µg/g weight, IP) on day 3 followed by 150 µg of rat anti-mouse anti-CD137Ab IP on day 4. Blood is collected on day 3 prior to rituximab treatment, on day 4 prior to anti-CD137Ab treatment, and on day 5 to assay NK cell expression of CD137, CD69, and CD16. Bioluminescent imaging is performed following IP luciferin injection (200 µL) on day 3 prior to Ab therapy and repeated weekly. The effect of CD137 with rituximab is shown in a disseminated human lymphoma xenotransplant model, shown in FIGS. 6A-6C.

Figure 7A:
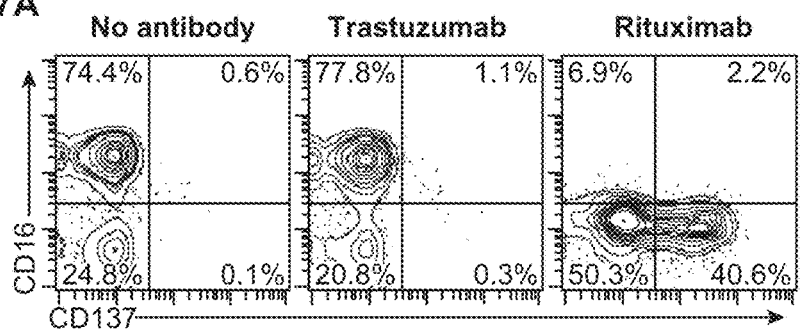
FIG. 7A-7C. Rituximab-coated, autologous lymphoma cells induce CD137 upregulation on NK cells from human patients with B cell malignancies. Peripheral blood from patients with B cell malignancies and circulating tumor cells (CTC) were analyzed for CD137 expression on CD3⁻CD56⁺ NK cells after 24 hour culture with media alone, trastuzumab, or rituximab (FIGS. 7A and 7B).
Figure 7B:
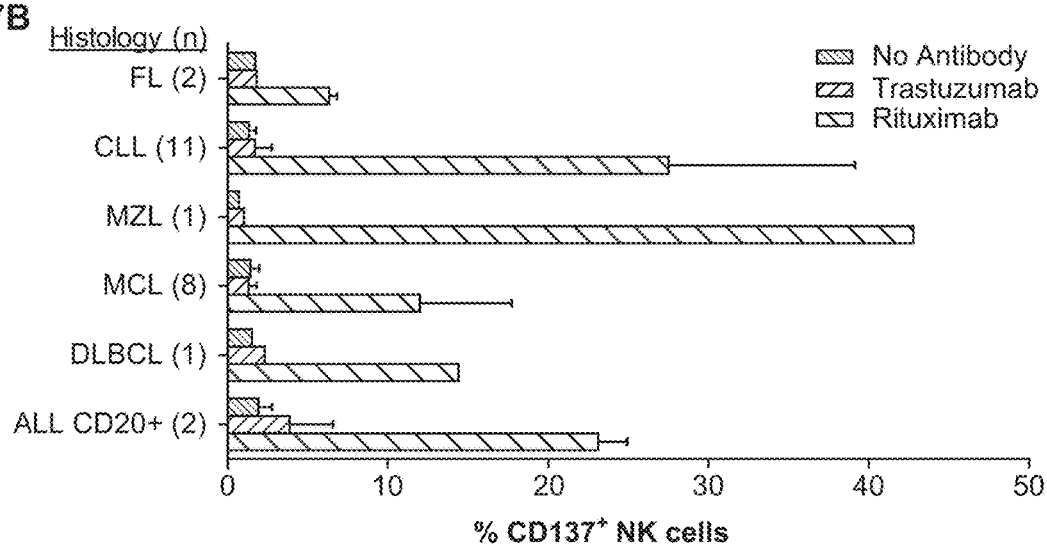
Figure 7C:
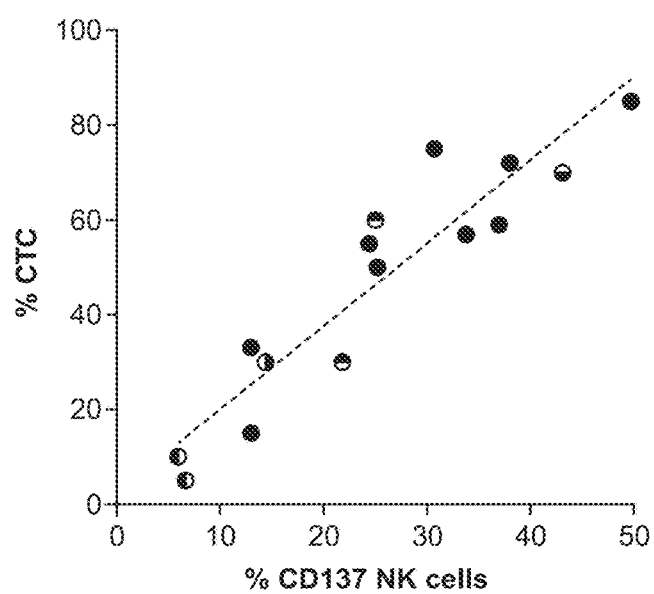
Figure 8C:
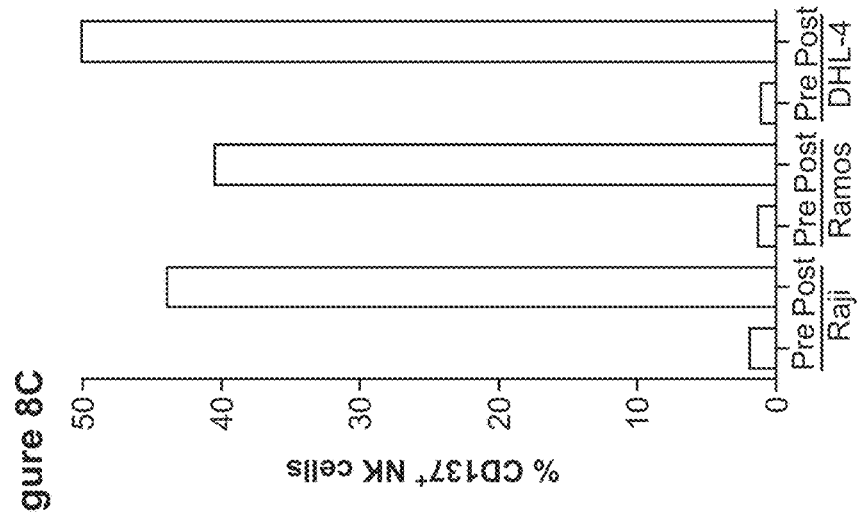
FIG. 8A-8C. CD137 induction and temporal expression on NK cells following preactivation. Purified NK cells from healthy donors were analyzed for CD137 expression after 24 hour culture with media, rituximab, trastuzumab, lymphoma cell lines (Raji, Ramos, DHL-4, or OCI-Ly19) and rituximab (FIG. 8A). Purified NK cells from a healthy donor were analyzed for CD137 expression after 0, 4, 16, 24, 48 and 72 hour culture with Raji cell line and rituximab (FIG. 8B). For experiments shown in FIG. 8C, peripheral blood mononuclear cells from a representative healthy donor were incubated with Raji, Ramos or DHL-4 and rituximab for 24 hours. Preactivated NK cells were then analyzed for CD137 expression (FIG. 8C) prior to performing the cytotoxicity assay.
Figure 8A:
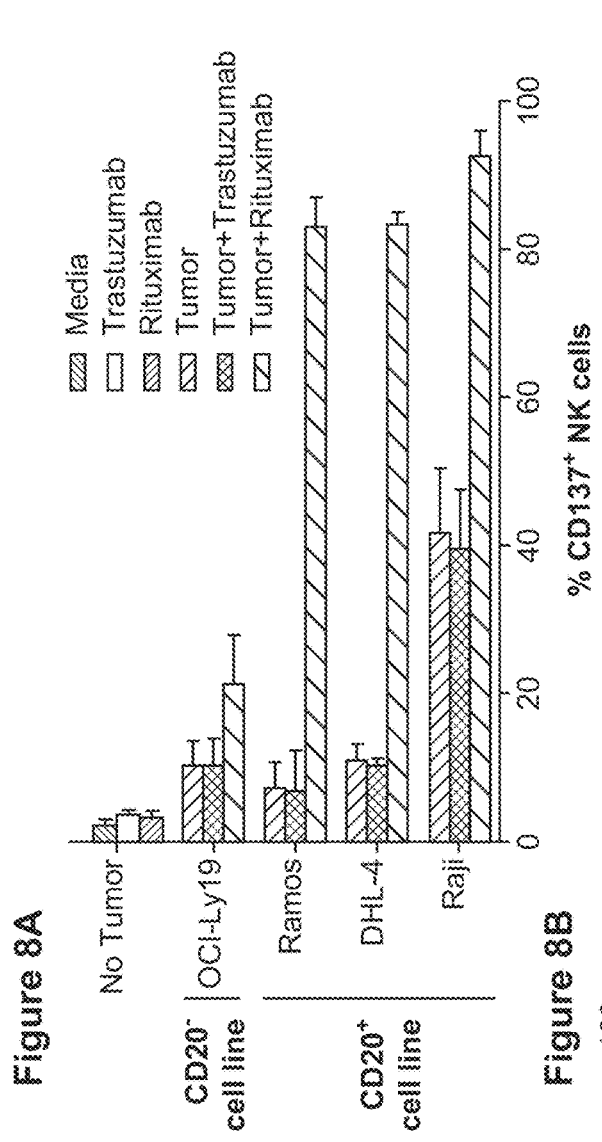
Figure 8B:
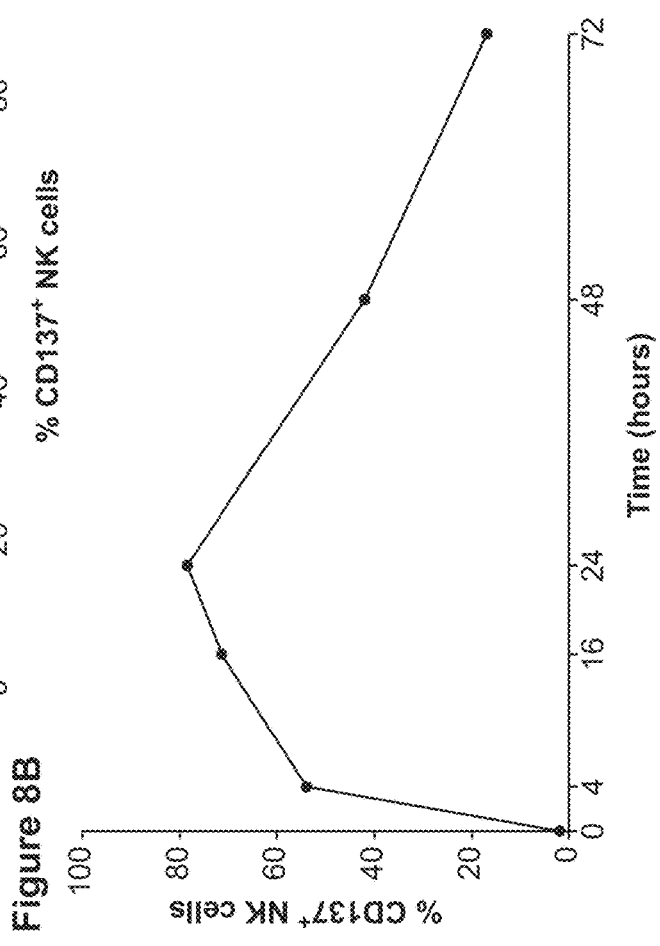

Rituximab-coated, autologous lymphoma cells induce CD137 upregulation on NK cells from human patients with B cell malignancies, shown in FIGS. 7A-7C. Peripheral blood from patients with B cell malignancies and circulating tumor cells (CTC) were analyzed for CD137 expression on $CD3^-CD56^+$ NK cells after 24 hour culture with media alone, trastuzumab, or rituximab. The kinetics of CD137 induction and temporal expression on NK cells following preactivation are analyzed in FIGS. 8A-8C.

Tumor growth was reduced by approximately 50% with either anti-CD20Ab or anti-CD137Ab monotherapy. However, all mice treated with anti-CD20Ab died before 60 days, and only 50% of mice treated with anti-CD137Ab were alive 100 days post-tumor inoculation. Treatment with anti-CD20Ab on day 3 followed by anti-CD137Ab on day 4 resulted in complete regression of tumor and survival at 100 days in 90% of mice. To determine if the observed synergy is dependent on NK cell function, NK cells were depleted with anti-asialo-GM1 on day −1, 0, and every 5 days thereafter till 20 days at which point a clear separation of treatment groups was observed. NK cell depletion with anti-asialo-GM1 abrogated the benefit of combination therapy.

Figure 10:
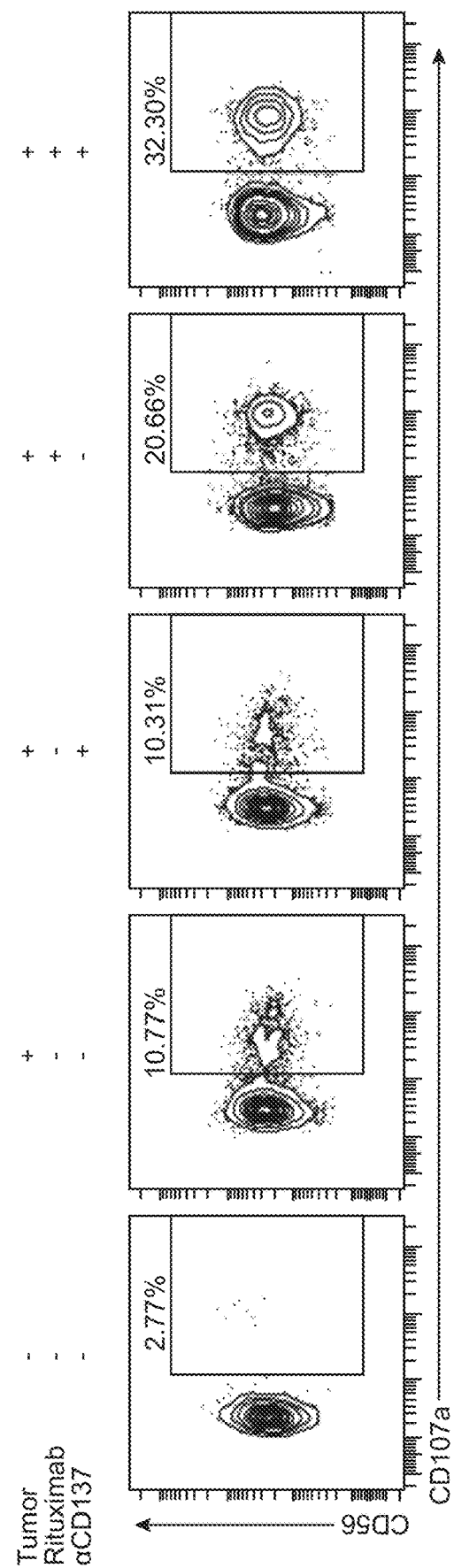
FIG. 10. Anti-CD137 agonistic mAb increases rituximab-mediated NK cell degranulation. NK cells isolated and purified from the peripheral blood of healthy donors were analyzed for degranulation by CD107a mobilization after 24 hour culture with media alone, CD20-positive lymphoma cell line (Raji, Ramos, or DHL-4), tumor and rituximab, tumor and anti-CD137 antibody, or tumor, rituximab, and anti-CD137 agonistic antibody. Representative flow cytometry plot of CD107a expression on NK cells after culture with Ramos.

Anti-CD137 agonistic mAb increases cytokine release and rituximab-mediated cytotoxicity of pre-activated NK cells, shown in FIGS. 9A-9B. To evaluate NK cell interferon-γ secretion purified NK cells were isolated from healthy PBMCs and cultured for 24 hours together with rituximab (10 µg/mL) and irradiated (5,000 rads) lymphoma tumor cells (Raji) at a ratio of 1:1. After 24 hours, NK cells were isolated and assessed for purity. Preactivated, purified NK cells were then cultured for 4 hours in media alone, or with anti-CD137 mAb alone, rituximab alone, or rituximab plus anti-CD137 mAbs and supernatant was harvested and analyzed by ELISA for interferon-γ. NK cell cytotoxicity on Raji tumor cells was analyzed in chromium release assay with and without prior NK cell preactivation. Anti-CD137 agonistic mAb also increases rituximab-mediated NK cell degranulation, shown in FIG. 10.

EXAMPLE 2

Figure 11:
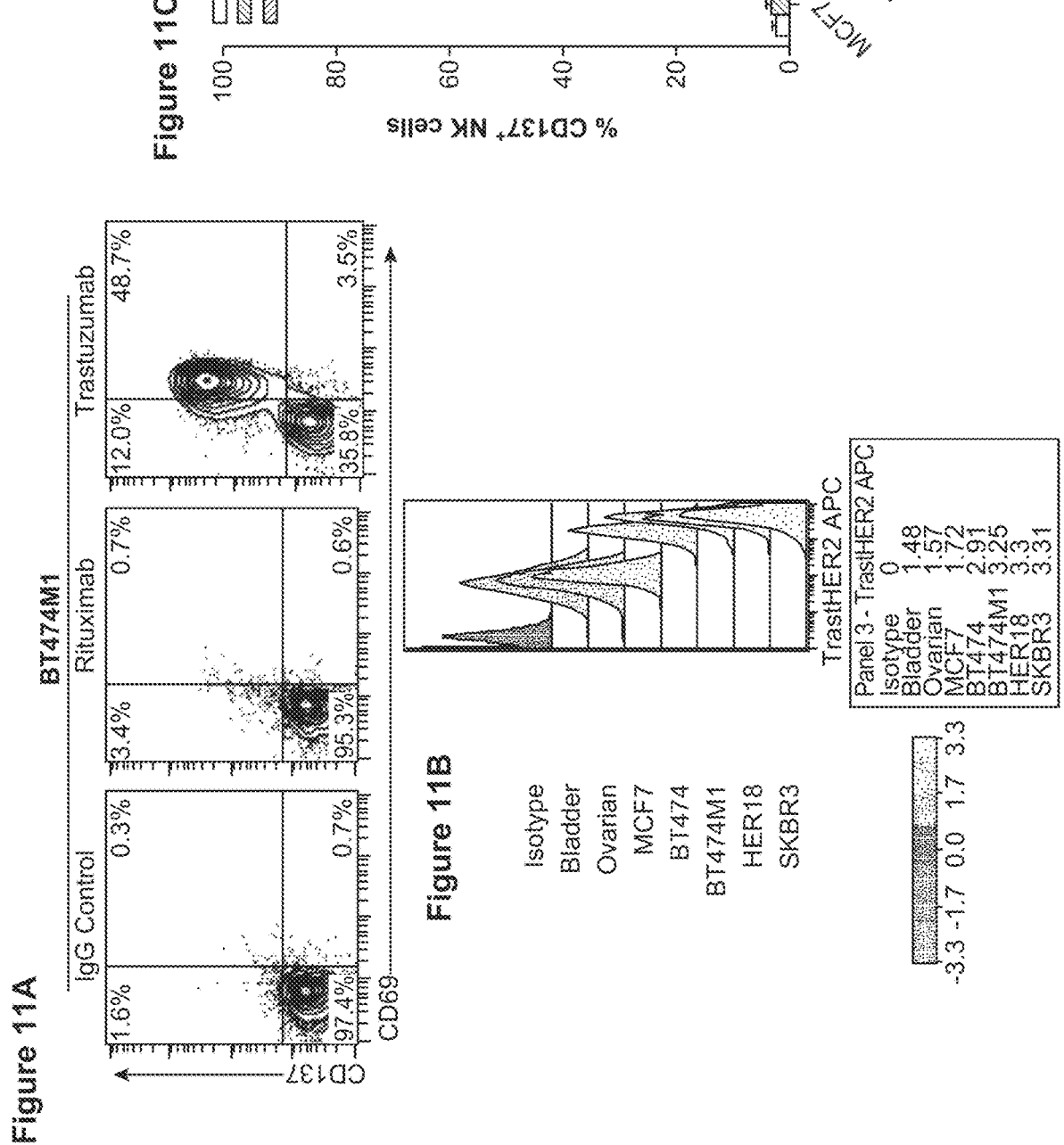
FIG. 11A-11C. Trastuzumab induces CD137 upregulation on human NK cells following incubation with HER2-positive tumor cells. Peripheral blood from three healthy donors was analyzed for CD137 expression on CD3$^-$CD56$^+$ NK cells after 24 hour culture with breast cancer cell lines and IgG control, trastuzumab or rituximab.

Increased NK cell expression of CD137 occurs following NK cell exposure to $HER2^{30}$ breast cancer coated with trastuzumab. We then determined if expression of CD137 is similarly increased on NK cells following their exposure to breast cancer coated with trastuzumab. We isolated NK cells from blood of healthy donors and added them to breast cancer cell lines including MCF7 (a non-HER2 expressing breast cancer cell line) and SKBR3 (a HER2 overexpressing breast cancer cell line) for 24 hours together with trastuzumab or rituximab. The NK cells were then analyzed by flow cytometry for CD137 expression, shown in FIG. 11.

NK cell expression of CD137 was determined following co-culture with appropriate tumor cell lines coated with cetuximab (10 µg/mL), rituximab (10 µg/mL) or trastuzumab (10 µg/mL) as detailed above for breast cancer cell lines. Flow cytometry for CD3 and CD56 was performed to evaluate purity of the NK cell isolation. Additional markers of activation including CD69, CD107, and CD16 were included in the flow cytometry panel. The colon cancer cell lines include HCT-8 ($EGFR^+$) and SW620 (EGFR), and the squamous head and neck cancer cell lines include TE3 ($EGFR^+HER2^-$) and TE4 ($EGFR^-HER2^+$).

Figure 12:
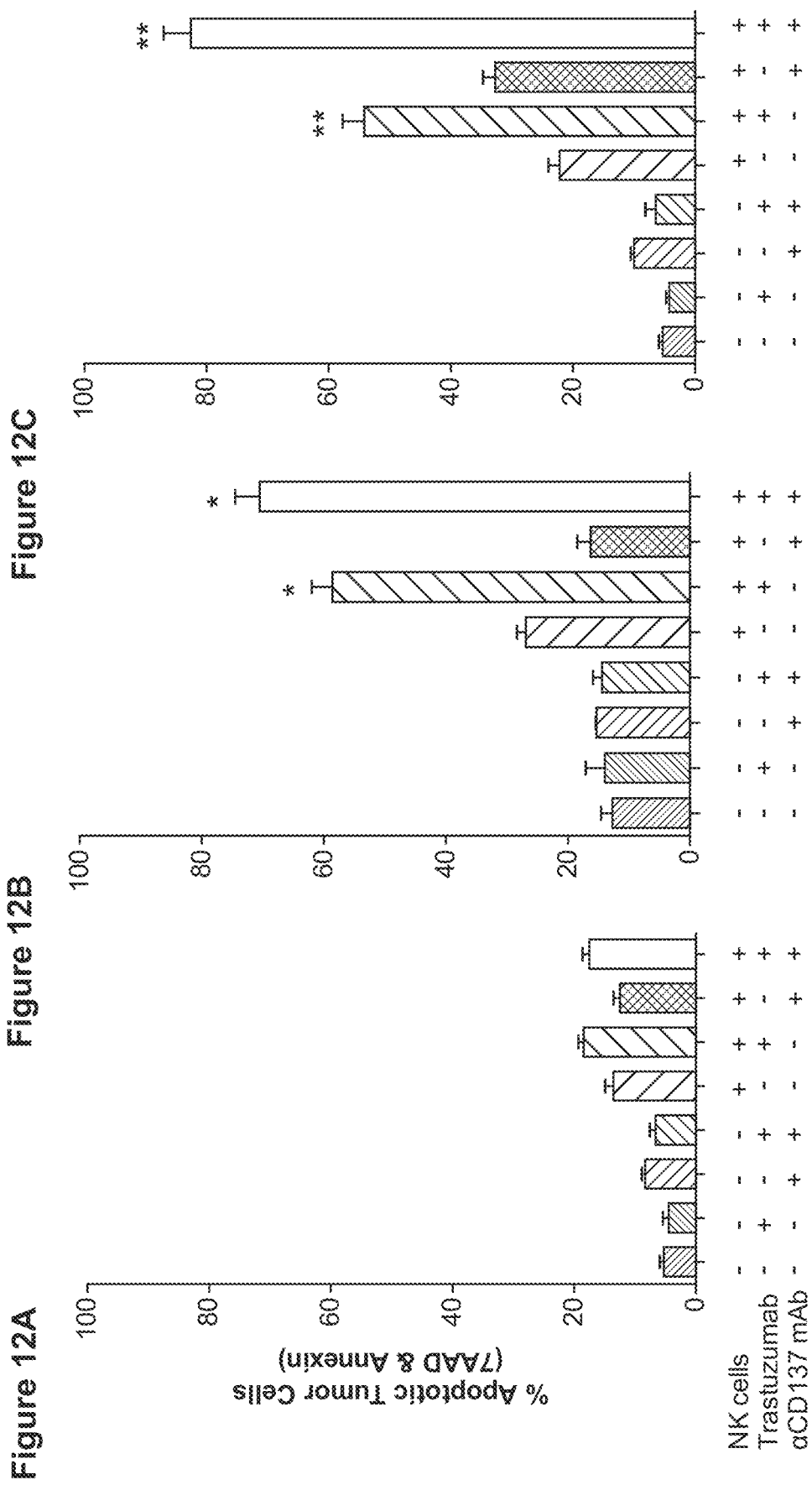
FIG. 12A-12C. Anti-CD137 agonistic mAb increases trastuzumab-mediated NK cell cytotoxicity on tumor cells as assayed by cell viability. Preactivated NK cells were purified before being incubated with MCF7, BT474M1, and HER18 for 18 hours.
Figure 13:
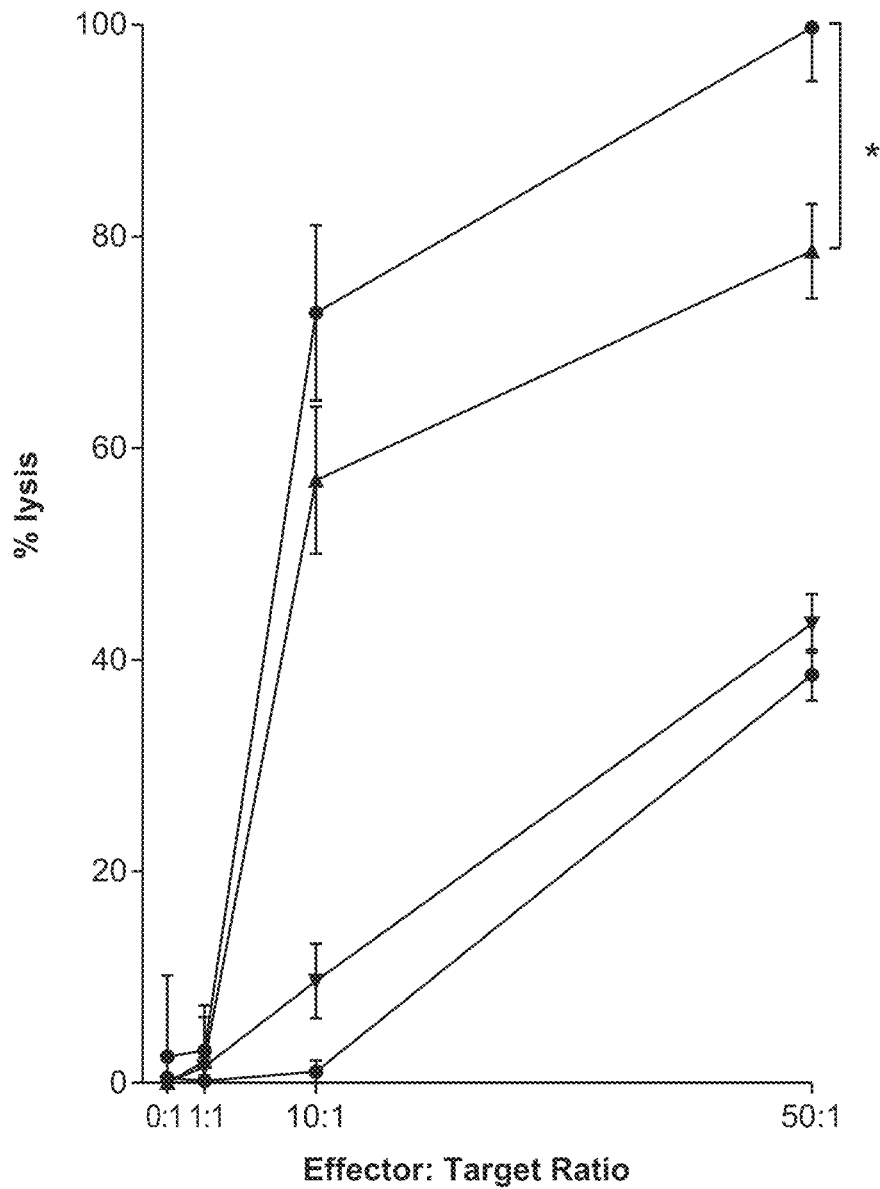
FIG. 13. Anti-CD137 agonistic mAb increases trastuzumab-mediated NK cell cytotoxicity on tumor cells as assayed by chromium release. NK cell cytotoxicity on BT474M1 tumor cells was analyzed in chromium release assay. Preactivated NK cells were purified before being incubated with chromium labeled BT474M1 cells for 4 hours. Shown is percent lysis of target cells by chromium release at varying effector (activated NK cells):target (BT474M1) cell ratios cultured with media alone (●), anti-CD137 (▼), rituximab (▲), or rituximab and anti-CD137 (♦) antibodies (p=0.006).

As shown in FIGS. 12A-12C, anti-CD137 agonistic mAb increases trastuzumab-mediated NK cell cytotoxicity on tumor cells as assayed by cell viability. Preactivated NK cells were purified before being incubated with MCF7, BT474M1, and HER18 for 18 hours, and apoptosis evaluated The functional capacity of activated NK cells following their stimulation with antibody and tumor cells was also determined by chromium release assays. To investigate activity against HER2$^+$ breast cancer, NK cells isolated from normal blood were activated by co-culture with SKBR3 (HER2$^+$) and trastuzumab. These exposed NK cells were tested by flow cytometry for CD137 and CD69 expression to evaluate their activation. Activated NK cells are added to chromium labeled SKBR3 target cells at ratios of 12.5:1, 25:1, 50:1, and 100:1 together with trastuzumab (10 μg/mL), anti-CD137Ab (10 μg/mL), or trastuzumab+anti-CD137Ab (both at 10 μg/mL). A similar activation and killing assay is performed to investigate in-vitro functional activity against EGFR$^+$ colon cancer with HCT-8 (EGFR$^+$) cell line and cetuximab, and EGFR$^+$ head and neck cancers with TE3 (EGFR$^+$HER2$^-$) cell line and cetuximab. Shown in FIG. 13, anti-CD137 agonistic mAb increases trastuzumab-mediated NK cell cytotoxicity on tumor cells as assayed by chromium release.

Supporting evidence has been provided in a syngenic murine lymphoma model, anti-CD137 agonistic mAb enhances anti-breast cancer activity of trastuzumab in-vivo. As shown in FIGS. 14A-14B. Nu/nu nude mice were inoculated with 5×10$^6$ BT474M1 breast tumor cells, subcutaneously, on the abdomen 1 day after subcutaneous injection of 0.72 mg/60 day release beta-estradiol pellet. Post-tumor inoculation, mice then received either rat IgG control on day 3, trastuzumab antibody on day 3, anti-CD137 antibody on day 4, or trastuzumab on day 3 and anti-CD137 antibody on day 4 with each treatment repeated weekly for a total of three weeks. Mice were then monitored for tumor growth and overall survival.

Figure 15A:
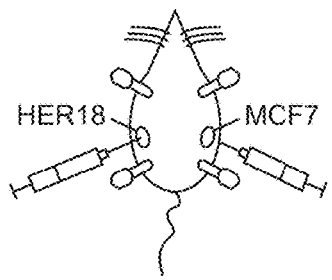
FIG. 15A-15C. Anti-CD137 agonistic mAb enhances anti-breast cancer activity of trastuzumab in-vivo while retaining HER2 specificity. Nu/nu nude mice were inoculated with 5×10$^6$ MCF7 breast tumor cells, subcutaneously, on the left flank, and 5×10$^6$ HER18 breast tumor cells, subcutaneously, on the right flank 1 day after subcutaneous injection of 0.72 mg/60 day release beta-estradiol pellet.
Figure 15B:
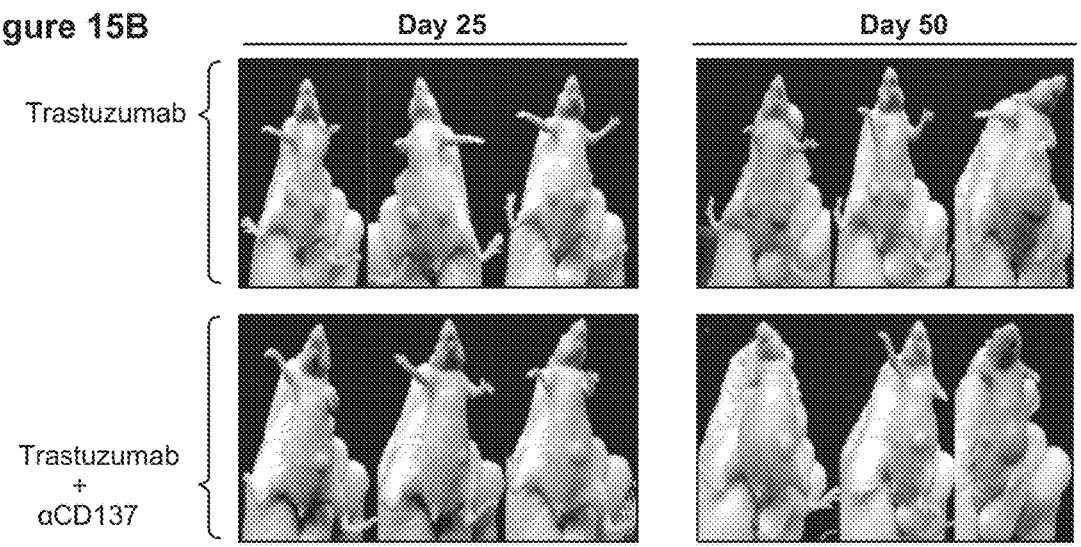
Figure 15C:
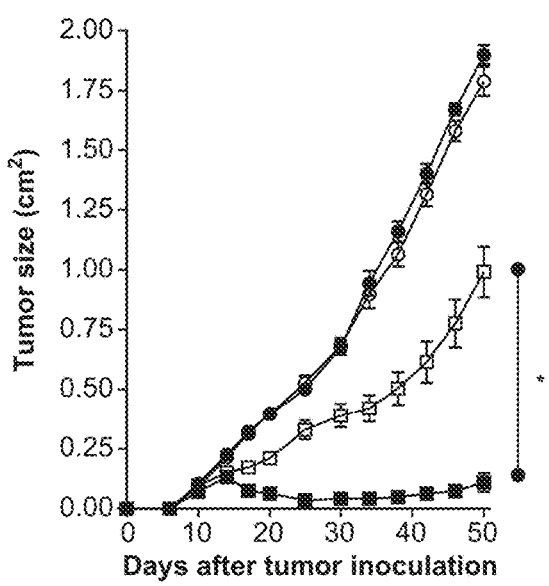
Figure 16:
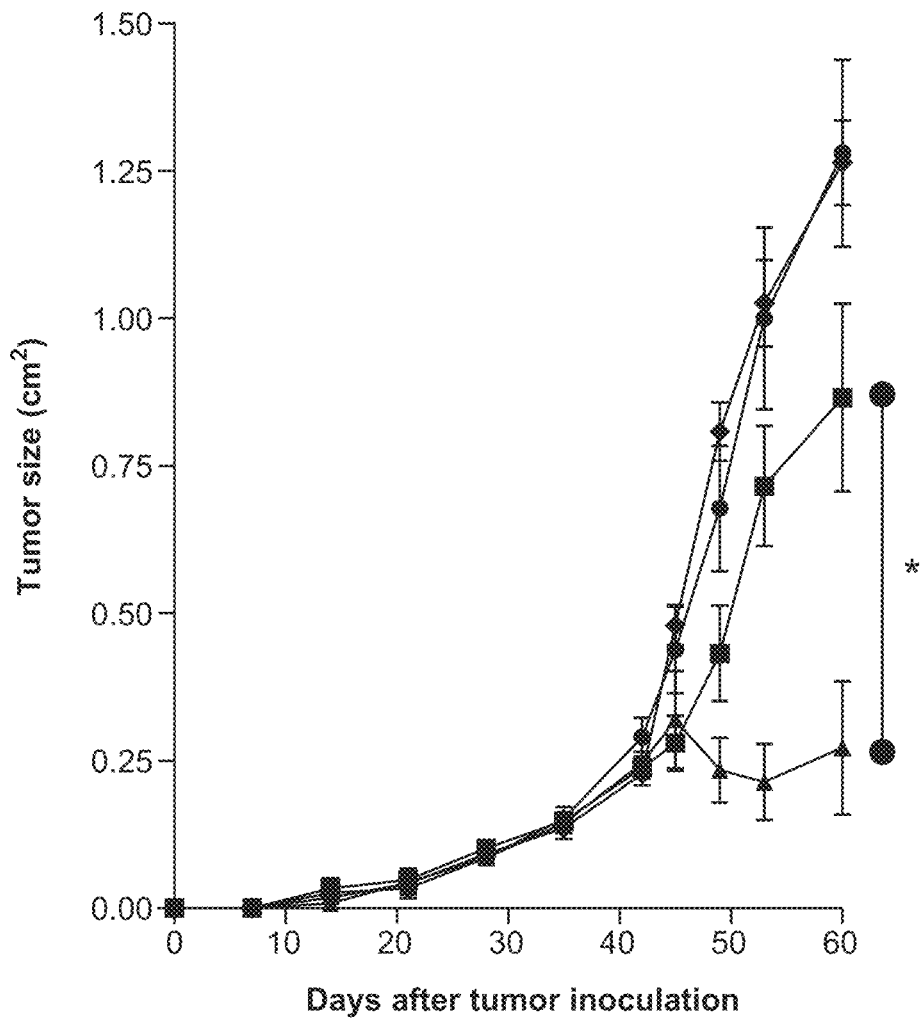
FIG. 16. Anti-CD137 agonistic mAb enhances anti-breast cancer activity of trastuzumab in-vivo against HER2$^+$ primary breast tumor. SCID mice were inoculated with 1×10$^6$ HER2$^+$ primary breast tumor cells by intramammary injection 24 hours after 200 cGy total body irradiation (TBI). On day 40 mice were randomized to one of four groups (5 mice per group) including IgG control with treatment on day 40 (●), trastuzumab on day 40 (■), anti-CD137 mAb on day 41 (♦), or trastuzumab on day 40 and anti-CD137 mAb on day 41 (▲). Treatment was repeated weekly in each group for a total of three treatments. Mice were monitored for tumor growth (*p=0.016).

As shown in FIG. 15A-15C, anti-CD137 agonistic mAb enhances anti-breast cancer activity of trastuzumab in-vivo while retaining HER2 specificity. Nu/nu nude mice were inoculated with 5×10$^6$ MCF7 breast tumor cells, subcutaneously, on the left flank, and 5×10$^6$ HER18 breast tumor cells, subcutaneously, on the right flank 1 day after subcutaneous injection of 0.72 mg/60 day release beta-estradiol pellet. Post-tumor inoculation, mice then received either trastuzumab on day 3, or trastuzumab on day 3 and anti-CD137 antibody on day 4 with each treatment repeated weekly for a total of three weeks. Representative mice were then monitored for tumor growth Anti-CD137 agonistic mAb enhances anti-breast cancer activity of trastuzumab in-vivo against HER2$^+$ primary breast tumor, as shown in FIG. 16. SCID mice were inoculated with 1×10$^6$ HER2$^+$ primary breast tumor cells by intramammary injection 24 hours after 200 cGy total body irradiation (TBI). On day 40 mice were randomized to one of four groups including IgG control with treatment on day 40, trastuzumab on day 40, anti-CD137 mAb on day 41, or trastuzumab on day 40 and anti-CD137 mAb on day 41. Treatment was repeated weekly in each group for a total of three treatments. Mice were monitored for tumor growth.

EXAMPLE 3

Figure 17A:
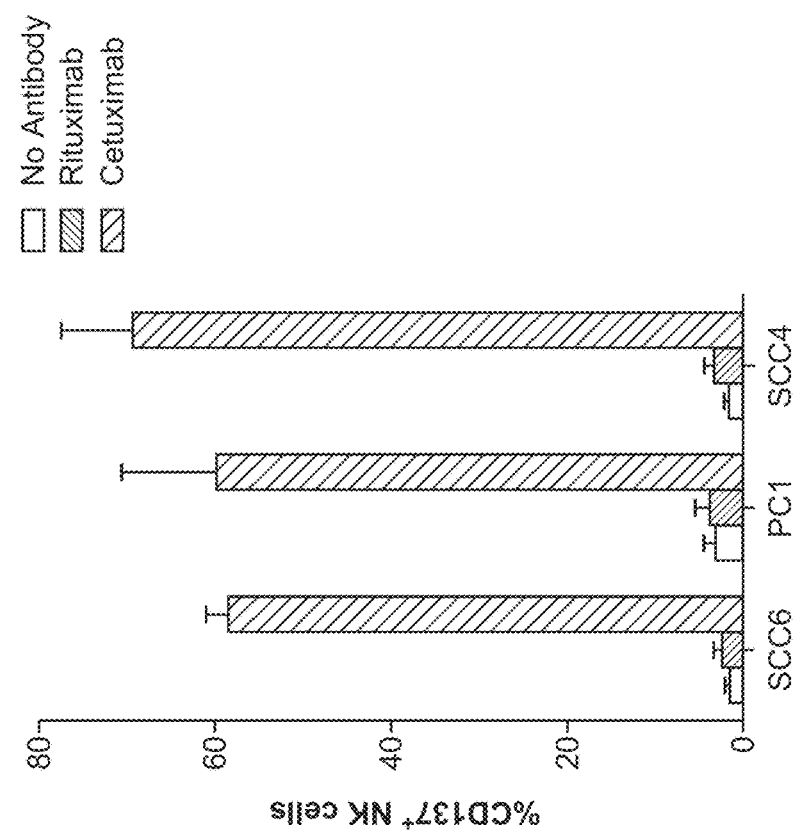
FIG. 17A-17B. Cetuximab induces CD137 upregulation on human NK cells following incubation with EGFR-positive tumor cells. Peripheral blood from three healthy donors was analyzed for CD137 expression on CD3$^-$CD56$^+$ NK cells after 24 hour culture with head and neck cancer cell lines and media alone, rituximab or cetuximab.
Figure 17B:
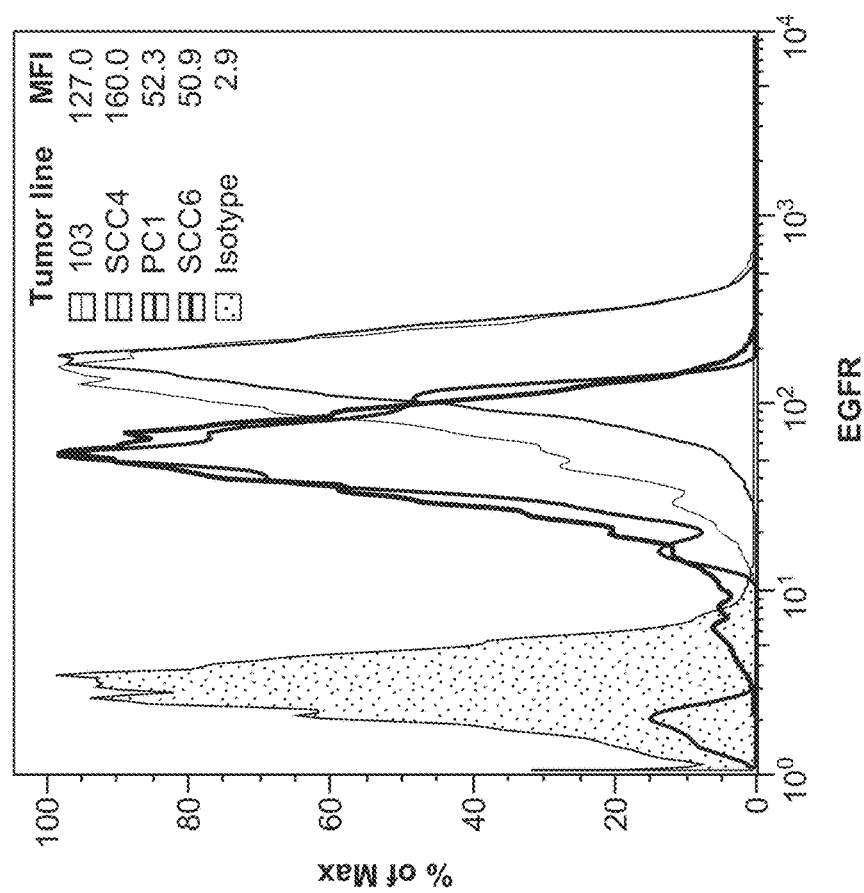

Cetuximab induces CD137 upregulation on human NK cells following incubation with EGFR-positive tumor cells, as shown in FIGS. 17A-17B. Peripheral blood from three healthy donors was analyzed for CD137 expression on CD3$^-$CD56$^+$ NK cells after 24 hour culture with head and neck cancer cell lines and media alone, rituximab or cetuximab, and shown to have increased expression.

As shown in FIGS. 18A-18C, anti-CD137 agonistic mAb increases cetuximab-mediated NK cell cytotoxicity on tumor cells as assayed by cell viability. Preactivated NK cells were purified before being incubated with SCC6, PC1, and SCC4 for 24 hours. The percent of apoptotic target cells was determined by annexin and 7AAD viability staining after culture with tumor alone or tumor and NK cells with media, cetuximab, anti-CD137, cetuximab and anti-CD137 antibodies.

Figure 19:
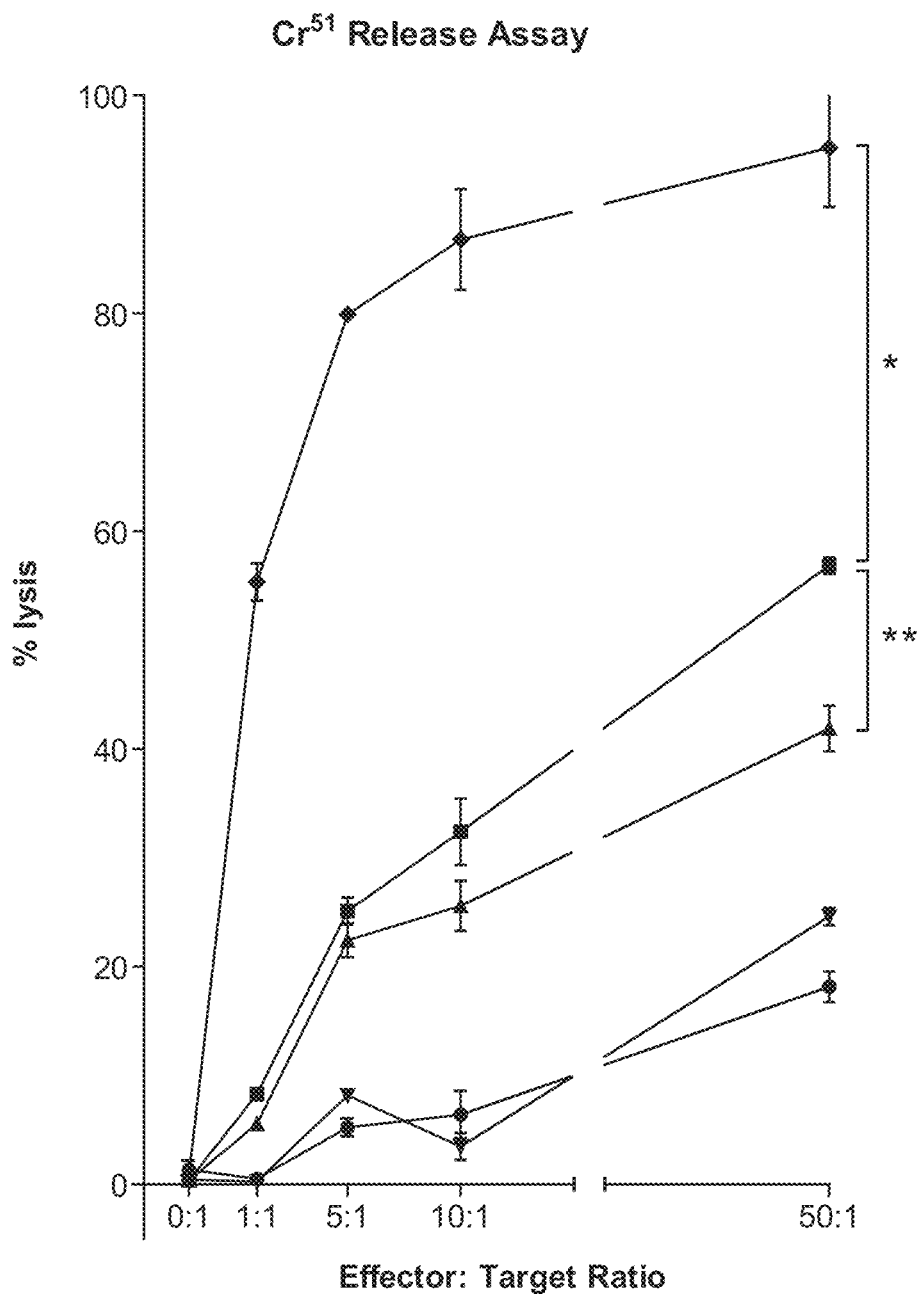
FIG. 19. Anti-CD137 agonistic mAb increases cetuximab-mediated NK cell cytotoxicity on tumor cells as assayed by chromium release. NK cell cytotoxicity on SCC6 tumor cells was analyzed in chromium release assay. Fresh and preactivated NK cells were purified before being incubated with chromium labeled SCC6 cells for 5 hours. Shown is percent lysis of target cells by chromium release at varying effector (fresh NK cells):target (SCC6) cell ratios cultured with media alone (●), anti-CD137 (▼), cetuximab (▲), or cetuximab and anti-CD137 (■) antibodies (**p=0.003) or preactivated NK cells as effectors with SCC6 targets and cetuximab and anti-CD137 (♦) antibodies (*p=0.002).

Anti-CD137 agonistic mAb increases cetuximab-mediated NK cell cytotoxicity on tumor cells as assayed by chromium release. NK cell cytotoxicity on SCC6 tumor cells was analyzed in chromium release assay. Fresh and preactivated NK cells were purified before being incubated with chromium labeled SCC6 cells for 5 hours. Shown in FIG. 19 is percent lysis of target cells by chromium release at varying effector (fresh NK cells):target (SCC6) cell ratios.

Figure 20:
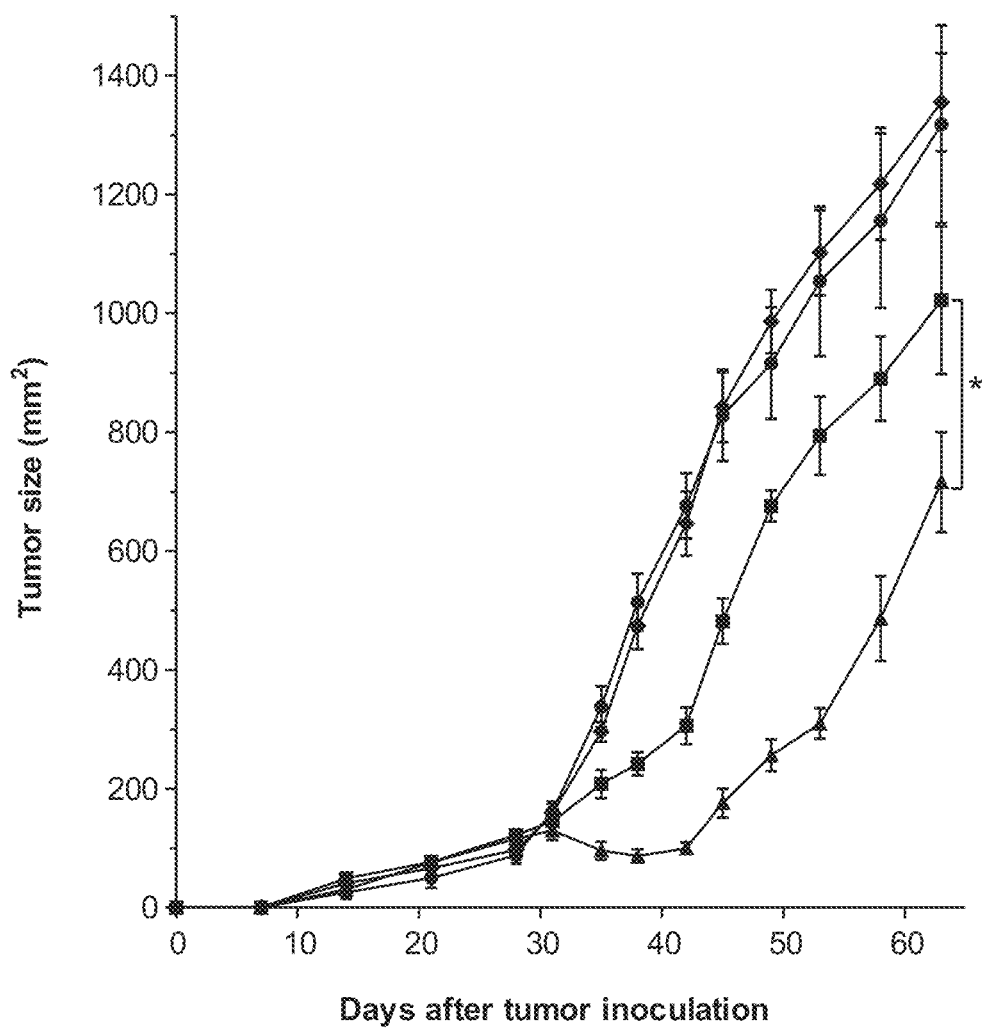
FIG. 20. Anti-CD137 agonistic mAb enhances anti-head and neck cancer activity of cetuximab in-vivo. Nu/nu nude mice were inoculated with $3 \times 10^6$ SCC6 head and neck tumor cells, subcutaneously, on the abdomen. Post-tumor inoculation, mice then received either rat IgG control on day 21 (●), cetuximab on day 21 (■), anti-CD137 antibody on day 22 (♦), or cetuximab on day 21 and anti-CD137 antibody on day 22 (▲) with each treatment repeated weekly for a total of three treatments. Mice (10 per group) were then monitored for tumor growth (A, *p<0.001).

Anti-CD137 agonistic mAb enhances anti-head and neck cancer activity of cetuximab in-vivo. Nu/nu nude mice were inoculated with 3×10$^6$ SCC6 head and neck tumor cells, subcutaneously, on the abdomen, shown in FIG. 20. Post-tumor inoculation, mice received either rat IgG control on day 21, cetuximab on day 21, anti-CD137 antibody on day 22, or cetuximab on day 21 and anti-CD137 antibody on day 22 with each treatment repeated weekly for a total of three treatments. Mice were then monitored for tumor growth.

Figure 21A:
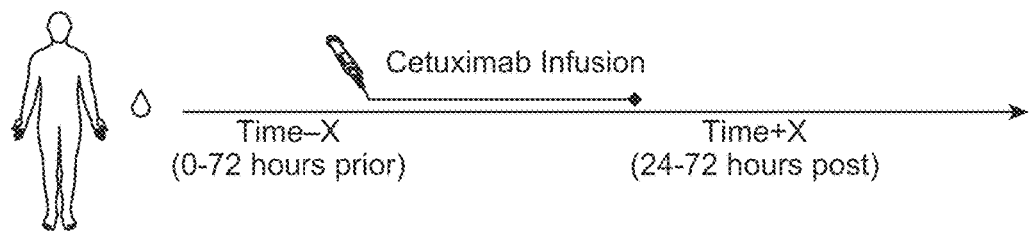
FIG. 21A-21B—Circulating NK cells upregulate CD137 following cetuximab infusion in patients with head and neck cancer. Fresh peripheral blood from patient with head and neck cancer was analyzed for CD137 expression on CD3⁻ CD56⁺ NK cells.
Figure 21B:
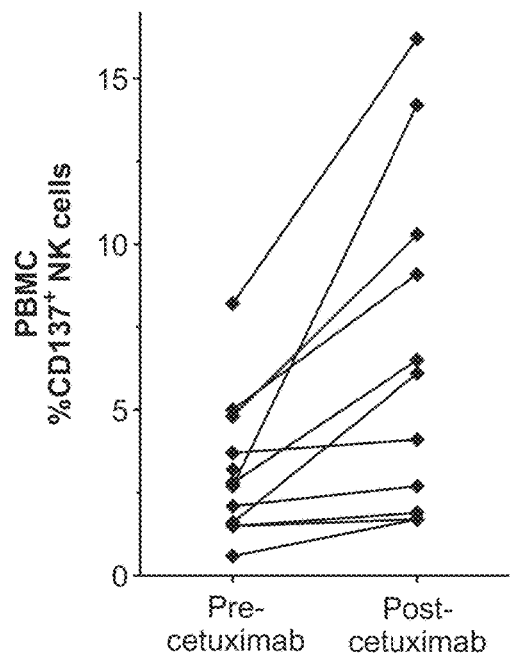

It was additionally shown that circulating NK cells upregulate CD137 following cetuximab infusion in patients with head and neck cancer (FIGS. 21A-21B). Fresh peripheral blood from patient with head and neck cancer was analyzed for CD137 expression on CD3$^-$CD56$^+$ NK cells, and shown to be upregulated.

The demonstration that an activation specific target (CD137) appears on NK cells after their exposure to antibody coated tumor cells, and that a second antibody against the CD137 target on these host cells has synergistic antitumor activity in multiple tumor models is innovative and of high impact to patient care. Agonistic anti-CD137 antibodies (for example BMS-663513) are currently in early-phase clinical trials, and in preclinical development by multiple major pharmaceutical companies. Approximately 300 patients have been treated in phase I and II trials with the BMS antibody. Negligible single agent activity has been observed with response rates less than 10%.

Based on our in vitro data, without concurrent tumor-targeted antibody such as rituximab no significant increase in NK cell function is observed. However, NK cell function is dramatically increased when both antibodies are combined. The present invention is of high importance as it has the opportunity to demonstrate the clinical value of anti-CD137 combination antibody therapy, despite minimal single agent activity in solid tumors. Therapy based on synergy through immunomodulation is an innovative and paradigm changing approach to improving the survival of patients with many types of cancer.

More broadly, we have observed that a number of other costimulatory molecules beside CD137, such as OX40 and GITR are up-regulated on NK cells following exposure to antibody-coated tumor cells. Similar to CD137, targeting of these inducible costimulatory molecules with agonistic antibodies are expected to stimulate and enhance NK cell function leading to increased ADCC.

What is claimed is:

1. A method of treating cancer, the method comprising:
   administering to an individual an antibody selective for a cancer cell antigen, and after a period of time sufficient to induce or upregulate expression of an inducible costimulatory molecule on NK cells;
   administering to said individual an agonist of said inducible costimulatory molecule in a dose effective to enhance NK cell antibody-dependent cellular cytotoxicity (ADCC);
   wherein the population of tumor cells in said patient is decreased.

2. The method of claim 1, wherein said inducible costimulatory molecule is one or more of CD137, OX40, GITR, CD30 and ICOS.

3. The method of claim 1, wherein said agonist is a monoclonal antibody.

4. The method of claim 3, wherein the antibody selective for a cancer cell antigen is specific for at least one of CD20, CD19, CD22, CD52, Her2, and epidermal growth factor receptor (EGFR).

5. The method of claim 1, wherein the method provides a synergistic effect in decreasing the population of tumor cells.

6. The method of claim 1, further comprising the step of measuring expression of said inducible costimulatory molecule on NK cells in said patient prior to administering said antibody selective for a cancer cell antigen and prior to administering said agonist, wherein said agonist is administered after an increase in expression of said inducible costimulatory molecule on NK cells.

7. The method of claim 1, wherein the cancer is a lymphoma.

8. The method of claim 1, wherein the cancer is a solid tumor.

9. The method of claim 8, wherein the solid tumor is a breast carcinoma.

10. The method of claim 8, wherein the solid tumor is a colon cancer.

11. The method of claim 8, wherein the solid tumor is a head and neck cancer.

12. The method of claim 1, wherein the antibody selective for a cancer cell antigen is specific for CD20.

13. The method of claim 1, wherein the antibody selective for a cancer cell antigen is specific for her-2.

14. The method of claim 1, wherein the antibody selective for a cancer cell antigen is specific for epidermal growth factor receptor (EGFR).

15. The method of claim 1, wherein the antibody selective for a cancer cell antigen is specific for CD52.

16. The method of claim 1, wherein the antibody selective for a cancer cell antigen is specific for CD19.

17. The method of claim 1, wherein the antibody selective for a cancer cell antigen is specific for CD22.

* * * * *